(12) United States Patent
Daum et al.

(10) Patent No.: US 9,861,619 B2
(45) Date of Patent: Jan. 9, 2018

(54) ANTIBIOTIC METHODS AND COMPOSITIONS FOR BACTERIA INFECTIONS

(71) Applicant: The University of Chicago, Chicago, IL (US)

(72) Inventors: Robert S. Daum, Chicago, IL (US); Susan Boyle-Vavra, Chicago, IL (US)

(73) Assignee: The University of Chicago, Chicago, IL (US)

( * ) Notice: Subject to any disclaimer, the term of this patent is extended or adjusted under 35 U.S.C. 154(b) by 74 days.

(21) Appl. No.: 14/439,850

(22) PCT Filed: Nov. 1, 2013

(86) PCT No.: PCT/US2013/068085
§ 371 (c)(1),
(2) Date: Apr. 30, 2015

(87) PCT Pub. No.: WO2014/071198
PCT Pub. Date: May 8, 2014

(65) Prior Publication Data
US 2015/0283120 A1    Oct. 8, 2015

Related U.S. Application Data

(60) Provisional application No. 61/721,310, filed on Nov. 1, 2012.

(51) Int. Cl.
| | |
|---|---|
| A61K 31/165 | (2006.01) |
| A61K 31/381 | (2006.01) |
| A61K 31/422 | (2006.01) |
| A61K 31/431 | (2006.01) |
| A61K 31/05 | (2006.01) |
| A61K 31/122 | (2006.01) |
| A61K 31/138 | (2006.01) |
| A61K 31/4709 | (2006.01) |
| A61K 31/496 | (2006.01) |
| A61K 31/7048 | (2006.01) |
| A61K 45/06 | (2006.01) |

(52) U.S. Cl.
CPC ............ *A61K 31/431* (2013.01); *A61K 31/05* (2013.01); *A61K 31/122* (2013.01); *A61K 31/138* (2013.01); *A61K 31/165* (2013.01); *A61K 31/381* (2013.01); *A61K 31/422* (2013.01); *A61K 31/4709* (2013.01); *A61K 31/496* (2013.01); *A61K 31/7048* (2013.01); *A61K 45/06* (2013.01)

(58) Field of Classification Search
CPC .. A61K 31/431; A61K 31/165; A61K 31/381; A61K 31/422
See application file for complete search history.

(56) References Cited

U.S. PATENT DOCUMENTS

| | | | |
|---|---|---|---|
| 3,272,701 A | 9/1966 | Kaitz et al. | 424/116 |
| 2004/0244713 A1* | 12/2004 | Manzotti | A23L 3/3526 119/231 |
| 2007/0258996 A1 | 11/2007 | Mookerjee et al. | |
| 2010/0234348 A1 | 9/2010 | Cottarel et al. | |
| 2012/0064125 A1* | 3/2012 | Horswill | A61K 38/08 424/400 |

FOREIGN PATENT DOCUMENTS

| | | |
|---|---|---|
| EP | 1149580 | 10/2001 |
| EP | 2243482 | 10/2010 |
| FR | 2645018 | 10/1990 |
| WO | WO 0051588 | 9/2000 |
| WO | WO 2012032360 | 3/2012 |
| WO | WO 2013103780 | 7/2013 |

OTHER PUBLICATIONS

Boyle-Vavra et al., "VraT/YvqF is required for methicillin resistance and activation of the VraSR regulon in *Staphylococcus aureus*," *Antimicrob Agents Chemother*. 57(1):83-95, 2010.
Brown et al., "Pharmacokinetics of norfloxacin in dogs after single intravenous and single and multiple oral administrations of the drug," *Am. J. Vet. Res.*51(7):1065-1070, 1990.
Drugs.com, "Nafcillin," https://web.archive.org/web/20100328053716/http://www.drugs.com/pro/nafcillin.html, 2010. Retrieved Jan. 1, 2014.
Drugs.com, "Oxacillin Injection," https://web.archive.org/web/20120206070325/http://www.drugs.com/pro/oxacillin-injection.html, 2012. Retrieved Jan. 1, 2014.
International Search Report and Written Opinion for PCT/US2013/068085, dated Jan. 16, 2014.

(Continued)

*Primary Examiner* — Yong Chong
(74) *Attorney, Agent, or Firm* — Norton Rose Fulbright US LLP

(57) ABSTRACT

Compositions and methods are provided for treating or inhibiting a bacterial infection involving at least one antibiotic and a compound that potentiates the antibiotic activity of the antibiotic. In certain embodiments the antibiotic is a beta lactam. In further embodiments, the antibiotic is oxacillin. In additional embodiments, the potentiating compound is an inhibitor of vraSR operon expression. In specific embodiments, the bacterial infection involves an antibiotic-resistant bacteria.

15 Claims, 9 Drawing Sheets

(56) References Cited

OTHER PUBLICATIONS

Merck, "Noroxin (Norfloxacin)," https://web.archive.org/web/20120415000000*/http://www.merck.com/product/usa/pi_circulars/n/noroxin/noroxin_pi.pdf, 2012. Retrieved Dec. 30, 2013.
Rohner et al., "Synergistic effect of quinolones and oxacillin on methicillin-resistant *Staphylococcus* species," *Antimicroh. Agents Chemother.* 33(12):2037-2041, 1989.
Waltho and Williams, "Aspects of molecular recognition: solvent exclusion and dimerization of the antibiotic ristocetin when bound to a model bacterial cell-wall precursor," *J. Am. Chem. Soc.* 111:2475-2480, 1989.
Williams and Waltho, "Molecular basis of the activity of antibiotics of the vancomycin group," *Biochem. Pharmacology* 37(1):133-141, 1988.
Extended European Search Report and Opinion for EP13850898.1, dated Jun. 28, 2016.
Notice of Reasons for Rejection for JP2015-540824, dated Jul. 19, 2017.
Boyce et al., *Antimicrobial Agents and Chemotherapy* 39.6: 1324-1328 (1995).
Broun et al., *Antimicrobial Agents and Chemotherapy* 38.3: 576-579 (1994).
Gulden et al., *Chemotherapy* 34: 117-126 (1988).
Hall et al., *J. Lab. & Clin. Med.* 56: 83-104 (1960).
Neu et al., *Antimicrobial Agents and Chemotherapy* 25.6: 687-689 (1984).
Rhee et al., *J. Korean Soc. Microbiol.* 30: 23-36 (1995).
Tone et al., *The Japanese Journal of Antibiotics* 29.5: 559-570 (1976).
Uno, Yoshifumi, *The Journal of the Japanese Association for Infectious Diseases* 73.4: 291-297 (1999).

* cited by examiner

ANTIBIOTIC METHODS AND COMPOSITIONS FOR BACTERIA INFECTIONS

CROSS-REFERENCE TO RELATED APPLICATION

This application is a national phase application under 35 U.S.C. §371 of International Application No. PCT/US2013/068085, filed Nov. 1, 2013, which claims the benefit of priority to U.S. Provisional Application No. 61/721,310, filed Nov. 1, 2012. The entire contents of each of the above-referenced disclosures are specifically incorporated herein by reference without disclaimer.

BACKGROUND OF THE INVENTION

1. Field of the Invention

The present invention relates generally to the field of medicine. More particularly, it concerns the use of chemical compounds that inhibit the vraSR operon and potentiate the action of antibiotics.

2. Description of Related Art

*Staphylococcus aureus* is a well-adapted human parasite that is both a commensal and an important pathogen. It is responsible for a wide variety of infectious diseases that range from minor skin abscesses to severe infections and toxinoses requiring hospitalization. *Staphylococcus aureus* strains resistant to nearly all beta-lactams, so-called methicillin-resistant *Staphylococcus aureus* (MRSA), are a leading cause of healthcare associated and, since the 1990s, community-associated infection. An epidemic of MRSA infections has enhanced the urgency to identify alternative antibacterial agents for successful treatment. Unfortunately, this need comes at a time when the industry-driven pipeline for antibacterial development has slowed.

SUMMARY OF THE INVENTION

Methods and compositions are provided for inhibiting, preventing, or treating a bacterial infection, particularly bacteria that rely on a vraSR operon for signal transduction. This operon is conserved among *Staphylococcus aureus* strains and methods and embodiments concern staphylococcal bacterial infections. In particular, methods and compositions involve an antibiotic and a compound that can be qualified as potentiating the activity of the antibiotic and/or an inhibitor of vraSR operon expression or activity.

In some embodiments, there are methods for inhibiting a *staphylococcus* infection comprising administering to a subject having a *staphylococcus* infection or at risk of a *staphylococcus* infection: (a) an antibiotic, and (b) an antibiotic potentiator, wherein the antibiotic potentiator is a compound selected from the group consisting of clomifene, gossypol, menadione and pyrvinium, or a prodrug or salt thereof.

In additional embodiments, there are methods for inhibiting a *staphylococcus* infection comprising administering to a subject: (a) an antibiotic, and (b) a compound selected from the group consisting of clomifene, gossypol, menadione and pyrvinium, or a prodrug or salt thereof. In still further embodiments, there are methods for inhibiting a *staphylococcus* infection comprising administering to a subject: (a) an antibiotic, and (b) a compound selected from the group consisting of oleandomycin and norfloxacin, or a prodrug or salt thereof.

In particular embodiments, methods and compositions specifically concern clomifene or a prodrug or salt thereof.

In other embodiments, methods and compositions involve gossypol, or a prodrug or salt thereof. In further embodiments, methods and compositions include menadione, or a prodrug or salt thereof. In additional embodiments, methods and compositions comprise pyrvinium, or a prodrug or salt thereof. It is specifically contemplated that one or more of clomifene, gossypol, menadione or pyrvinium, or a prodrug or salt thereof, may be excluded from methods and compositions discussed herein. In still further embodiments, methods and compositions include an antibiotic as the antibiotic potentiator. In certain embodiments, an antibiotic potentiator that is an antibiotic is oleandomycin, or a prodrug or salt thereof. In other embodiments, methods and compositions methods and compositions include norfloxacin, or a prodrug or salt thereof; norfloxacin is an antibiotic that is also an antibiotic potentiator in some embodiments. It is specifically contemplated that one or more of oleandomycin or norfloxacin, or a prodrug or salt thereof, may be excluded from methods and compositions discussed herein.

Other methods involve treating a patient with a *staphylococcus* infection comprising administering to the patient an antibiotic and administering to the patient clomifene, gossypol, menadione or pyrvinium, or a prodrug or salt thereof.

Further embodiments concern methods for treating a patient with a *staphylococcus* infection comprising administering to the patient an effective amount of an antibiotic and an effective amount of clomifene, gossypol, menadione or pyrvinium, or a prodrug or salt thereof.

In some embodiments, methods and compositions concern an antibiotic that is a beta-lactam antibiotic. In certain embodiments, the antibiotic is a penicillinase-resistant beta-lactam antibiotic. In further embodiments, the penicillinase-resistant beta-lactam antibiotic is oxacillin. Certain embodiments concern a penicillinase-resistant beta-lactam antibiotic that is methicillin, nafcillin, cloxacillin, dicloxacillin or flucloxacillin. Other antibiotics for use in methods and compositions are discussed below. An antibiotic may be given before, with, or after an antibiotic potentiator is administered to the patient. The antibiotic and the antibiotic potentiator may or may not be formulated similarly. In some embodiments, they are co-formulated or are in the same composition or solution. In one example, one or both of them may be formulated for oral administration. In another example, they may both be formulated for i.v. administration. It is also contemplated that compounds may be administered to a subject by the same or different routes of administration.

Embodiments can be used with a subject that *staphylococcus* can infect, such as mammals, and particularly humans, monkeys, primates, apes, dogs, cats, cows, horses, pigs, goats, mice, or rats. In certain embodiments, the subject is a human patient. In particular methods, the subject has been tested for a *staphylococcus* infection. In other embodiments, the subject is or has been diagnosed with a *staphylococcus* infection. Methods may further involve testing or evaluating a patient for *staphylococcus* infection. In additional embodiments, methods also include diagnosing a patient for *staphylococcus* infection. In some cases, a subject is at risk of acquiring a *staphylococcus* infection. This includes, but is not limited to, patient undergoing an invasive hospital procedure (such as one requiring anesthesia) or surgery, patients having undergone an invasive hospital procedure or surgery, patients placed on an i.v., or patients on a ventilator. In certain embodiments, a subject has one or more symptoms of a staphylococcal infection.

In some methods, the subject has or is at risk for native valve endocarditis or prosthetic valve endocarditis. In other embodiments, the subject has or is at risk for joint infection, meningitis, osteomyelitis, pneumonia, septicemia, sinusitis, or skin or soft tissue infection. In further embodiments, the subject is administered about 2-3 g of oxacillin intravenously every 4 to 6 hours. In other methods, the subject is administered about 1-2 g of oxacillin intravenously or intramuscularly every 4 to 6 hours or about 500 mg to about 1 g of oxacillin orally every 4 to 6 hours.

In some cases, treating a *Staphylococcus* infection comprises reducing abscess formation or incidence or reducing bacterial load in the subject. In other embodiments, treating a *Staphylococcus* infection comprises reducing symptoms of any infection including but not limited to reducing fever, reducing swelling at the infection site, and/or reducing pain at the infection site.

With some methods and compositions, an infection is from a *staphylococcus* that belongs to the species *Staphylococcus aureus*. In certain embodiments, the *staphylococcus* infection is methicillin resistant *Staphylococcus aureus* (MRSA). In alternative embodiments, the *staphylococcus* infection is methicillin sensitive *Staphylococcus aureus* (MSSA), and the composition is provided to treat the infection while reducing the likelihood of acquisition of methicillin resistance.

Certain methods and compositions may involve a second antibiotic. In some embodiments, methods involve administering the second antibiotic. In particular cases, the second antibiotic is gentamicin or rifampin. Other second antibiotics are discussed below. Methods or compositions may also include a staphylococcal vaccine. Methods include, in particular embodiments, administering a staphylococcal vaccine. This may be administered before, after, or with an antibiotic and/or an antibiotic potentiator.

In some embodiments, the antibiotic is administered at a dose of about 0.1 mg/kg to about 50 mg/kg. In particular embodiments, the subject is a pediatric patient, which means under 18 years of age for a human patient. For a pediatric patient, in some embodiments an antibiotic is administered about 25 mg/kg to about 50 mg/kg intravenously or intramuscularly every 6 to 12 hours or about 12.5 mg/kg orally every 6 hours. In certain embodiments, the antibiotic is oxacillin.

Methods may also involve an antibiotic potentiator administered in a dose of 0.1 mg/kg to about 100 mg/kg.

In some methods administration of a compound to a subject is oral, sublingual, sublabial, gastrointestinal, rectal, epicutaneous (topical), intradermal, subcutaneous, nasal, intravenous, intraarterial, intramuscular, intracardiac, intraosseous, intrathecal, intraperitoneal, intravesical, intravitreal, intracavernous, intravaginal, intrauterine, epidural, intracerebral and/or intracerebroventricular. In specific embodiments, administration is topical, enteral, or parenteral. In some instances, administration is by application onto the skin, inhalation, an enema, eye drops, ear drops, absorption across mucosal membranes, the mouth, a gastric feeding tube, a duodenal feeding tube, a suppository, an injection into a vein, an injection into an artery, an injection into the bone marrow, an injection into muscle tissue, an injection into the brain, an injection into the cerebral ventricular system or an injection under the skin. It is also contemplated that compounds may be administered to a subject by the same or different routes of administration.

In some embodiments the antibiotic and the antibiotic potentiator are in the same composition. In other embodiments the antibiotic and the antibiotic potentiator are administered simultaneously in the same or different compositions. A subject is administered an antibiotic up to 24 hours prior to administration of the antibiotic potentiator in some cases. In others, the antibiotic potentiator is administered up to 24 hours prior to administration of the antibiotic. In some embodiments, the antibiotic and antibiotic potentiator are administered within 24 hours of each other.

Pharmaceutical compositions are also provided. In some embodiments, a pharmaceutical composition includes an antibiotic and a compound selected from the group consisting of clomifene, gossypol, menadione or pyrvinium, or prodrug or a salt thereof. In additional embodiments, a pharmaceutical composition includes a single unit dose of a selected antibiotic and a compound selected from the group consisting of clomifene, gossypol, menadione or pyrvinium.

In some cases, a pharmaceutical composition comprises at least an additional antibacterial agent. The additional antibacterial agent may be a further antibiotic, a staphylococcal vaccine composition or a polypeptide that specifically binds to a second staphylococcal protein. It is contemplated that the pharmaceutical composition may be a pill, capsule, tablet, lozenge, troche, solution, cream, gel, paste, liquid or solid. In embodiments where antibiotic and an antibiotic potentiator are in different compositions, each may be provided in one of these forms.

Additional embodiments concern a system for treating a bacterial infection comprising a pharmaceutically acceptable composition comprising an antibiotic and a pharmaceutically acceptable composition comprising an antibiotic potentiator that is clomifene, gossypol, menadione or pyrvinium. In some system embodiments, the antibiotic is in an aqueous formulation. Further embodiments involve a system in which the antibiotic is in an aqueous formulation that is an intravenous solution or an aqueous formulation that is injectable into the patient or into an intravenous solution. In other embodiments, an antibiotic potentiator is in an aqueous formulation. In certain cases, an antibiotic potentiator is in an aqueous formulation that is an intravenous solution or an aqueous formulation that is injectable into the patient or into an intravenous solution.

Embodiments discussed in the context of compositions may also be applied as methods, and vice versa.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Bacterial Growth Inhibition

Figure 1:
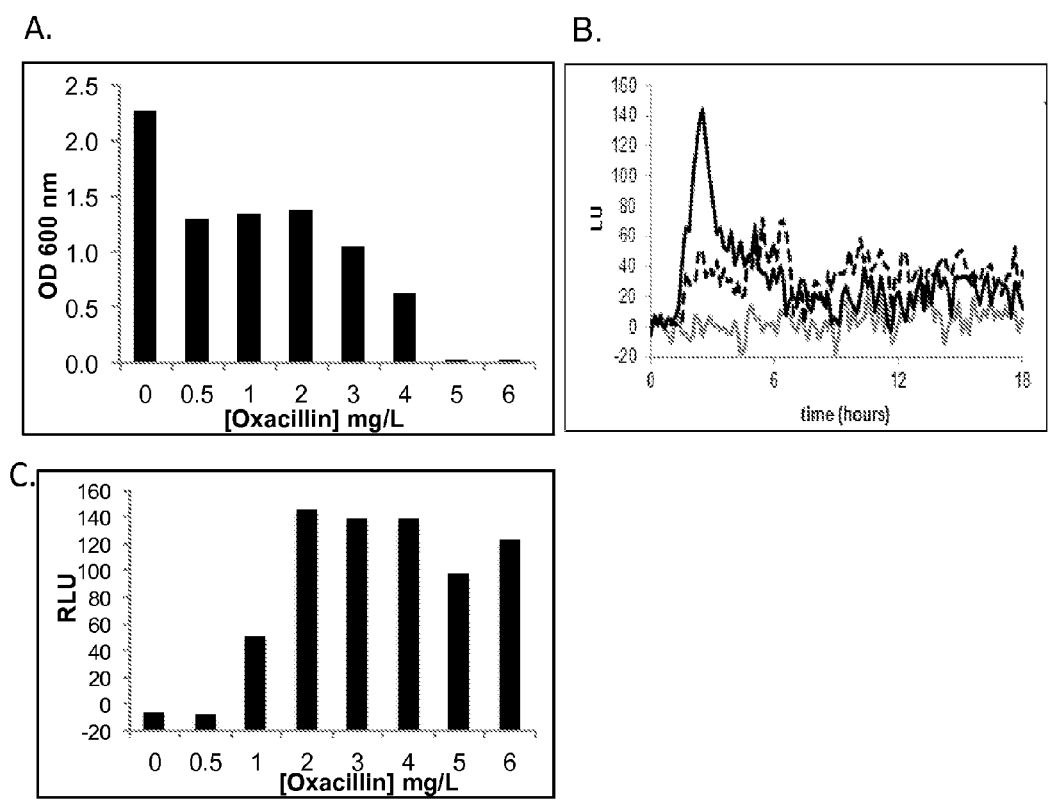
FIG. 1A-C: Optimal conditions for measuring growth and luminescence of the test strain, 923 pPvra-lux. (A) Absorbance at 18 hours as a function of oxacillin concentration. (B) Luminescence (LU) was monitored over 18 hours with oxacillin at 0 μg/mL (gray line), 1 μg/mL (dashed line), and 2 μg/mL (black solid line). (C) Luminescence at two hours post inoculation as a function of oxacillin concentration.

VraS and VraR constitute a two-component signal transduction system that requires a recently renamed third component, VraT (previously called YvqF) that is encoded on the same operon (1-3). The vraSR operon, conserved among Staphylococcus aureus strains, senses and responds to cell-wall stress elicited by clinically important antibacterials that work by interfering with bacterial cell wall synthesis. This vraSR operon is responsible for activation of a set of genes that presumably coordinately act together to adapt to cell wall stress. Compounds that inhibit expression of the vraSR operon are shown below to enhance the ability of a beta-lactam antibiotic to kill MRSA strains and treat infections caused by them (potentiation).

II. Antibiotics

Embodiments concern methods and compositions for treating bacterial infections, including infections involving antibiotic-resistant bacteria. Substances are provided that can be used in conjunction with antibiotics that are effective or potentially effective for treating or inhibiting a bacterial infection. The antibiotics specifically contemplated for use in embodiments include beta-lactam antibiotics. Some embodiments concern the use of one or more antibiotics in combination with one or more compounds that inhibit the vraSR operon. Further embodiments specifically contemplate the use of compounds that inhibit the vraSR operon together with one or more beta-lactam antibiotics. Yet further embodiments contemplate the use of compounds that inhibit the vraSR operon together with one or more antibiotics known to act via disruption of bacterial cell wall processes.

In some embodiments, Staphylococcus aureus is involved in the bacterial infection to be treated. Other embodiments contemplate the use of compounds that inhibit the vraSR operon against the homologous LiaRS system present in Bacillus subtilis, Streptococcus pneumoniae, and Streptococcus mutansi. Further embodiments contemplate the use of said compounds to target the homologous CesSR system in several Lactococcus species. Yet further embodiments contemplate the use of these compounds against other homologous two-component systems of cell-wall-mediated antibiotic resistance.

Certain embodiments contemplate the use of beta-lactam antibiotics. Beta-lactam antibiotics are a broad class of antibiotics, consisting of antibiotic agents that contain a beta-lactam nucleus in their molecular structures. This includes penicillin derivatives (penams), cephalosporins (cephems), monobactams, and carbapenems. Most beta-lactam antibiotics work by inhibiting cell wall biosynthesis in bacteria and are the most widely used group of antibiotics.

It is contemplated that compounds that inhibit the vraSR operon potentiate the action of any beta-lactam antibiotic. This group comprises any of Amoxicillin, Ampicillin, Pivampicillin, Hetacillin, Bacampicillin, Metampicillin, Talampicillin, Epicillin, Carbenicillin Carindacillin, Ticarcillin, Temocillin Azlocillin, Piperacillin, Mezlocillin Mecillinam Pivmecillinam, Sulbenicillin Clometocillin, Benzathine benzylpenicillin, Procaine benzylpenicillin, Azidocillin, Penamecillin, Phenoxymethylpenicillin, Propicillin, Benzathine phenoxymethylpenicillin, Pheneticillin, Cloxacillin, Dicloxacillin, Flucloxacillin, oxacillin, Meticillin, Nafcillin, Faropenem Biapenem, Ertapenem, Doripenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, cephamycin, Cefoxitin, Cefotetan, Cefmetazole, carbacephem, Loracarbef, Cefixime, Ceftriaxone, Ceftazidime, Cefoperazone, Cefcapene, Cefdaloxime, Cefdinir, Cefditoren, Cefetamet, Cefmenoxime, Cefodizime, Cefotaxime, Cefpimizole, Cefpiramide, Cefpodoxime, Cefsulodin, Cefteram, Ceftibuten, Ceftiolene, Ceftizoxime, oxacephem Flomoxef, Latamoxef, Cefepime, Cefozopran, Cefpirome, Cefquinome, Ceftobiprole, Ceftaroline fosamil, Ceftiofur, Cefquinome, Cefovecin, Aztreonam, Tigemonam, Carumonam or Nocardicin A. In embodiments using beta-lactamase sensitive antibiotics such as Amoxicillin, Ampicillin, pivampicillin, hetacillin, bacampicillin, metampicillin, talampicillin, epicillin, carbenicillin carindacillin, ticarcillin, temocillin azlocillin, piperacillin, mezlocillin mecillinam pivmecillinam, sulbenicillin clometocillin, benzathine benzylpenicillin, procaine benzylpenicillin, azidocillin, penamecillin, phenoxymethylpenicillin, propicillin, benzathine phenoxymethyl-penicillin, or pheneticillin, addition of a beta-lactamase inhibitor is further contemplated.

Further embodiments contemplate the use of other antibiotics that induce the cell wall stress stimulon (CWSS) in *Staphylococcus aureus* and. thus, involve vraSR such as fosfomycin, D-cycloserine, tunicamycin, bacitracin, bambermycin, vancomycin, moenomycin, teicoplanin, lysostaphin and daptomycin. In still further embodiments, the antibiotic is a cationic peptide such as cecropins, andropin, moricin, ceratotoxin, melittin, magainin, dermaseptin, bombinin, brevinin-1, esculentin and buforin II, CAP18, LL37, amide-modified ovispirin-1, and chlorpromazine.

Further embodiments contemplate the use of glycopeptide antibiotics related to vancomycin, including but not limited to ristocetin A and avoparcin. Still further embodiments contemplate the use of vancomycin derivatives and antibiotics of the vancomycin group, including but not limited to those referred to in Williams & Waltho, *J. Am. Chem. Soc.* 111:2475-80 (1994), and Williams & Waltho, *Biochem. Pharmacology* 37(1):133-31 (1988), which are hereby incorporated by reference.

In additional embodiments, compounds listed in Tables 9 and 10 are envisioned to be used as antibiotics, alone or in combination with the antibiotics or potentiators discussed herein.

In certain embodiments, it is contemplated that one or more of the antibiotics referred to herein can be excluded from being included in any embodiment described herein.

Penicillin G is administered in some embodiments to adults in doses ranging from 600,000 to >1,000,000 units. Penicillin G is administered in doses of 20-24 million units daily, in divided doses every 4-6 hours. For children, a dose of penicillin G is about 50,000 unis/kg/dose. One unit of penicillin G contains 0.6 µg of pure sodium penicillin G (i.e., 1 mg is 1667 units).

Amoxicillin may be administered to adults in doses ranging from 750 mg to 1.5 grams per day, in 3 divided doses. For children, doses of amoxicillin range from 20 to 40 mg/kg per day in 3 equally divided doses. Amoxicillin is also available in combination with clavulanic acid, a beta-lactamase inhibitor. A 250 mg dose of the combination drug amoxicillin/clavulanate will contain 250 mg of amoxicillin and either 125 or 62.5 mg of clavulanic acid. The combination is preferably administered to adults orally in doses of 750 mg per day divided into 3 equal doses every 8 hours, with a dose of 1.5 grams per day for severe infections, given in 3 equally divided doses. In children, the oral dose is 20 to 40 mg/kg per day in 3 equally divided doses.

In some embodiments ampicillin is administered to adults in doses of 6 to 12 grams per day for severe infections, in 3 to 4 equally divided doses. In children, the dose of ampicillin is 50 to 200 mg/kg per day in 3 to 4 equally divided doses. Larger doses of up to 400 mg/kg per day, for children, or 12 grams per day, for adults, may be administered. Ampicillin is also available in combination with sulbactam, a beta-lactamase inhibitor. Each 1.5 gram dose of ampicillin/sulbactam contains 1 gram of ampicillin and 0.5 grams of sulbactam. The combination is preferably administered to adults in doses of 6 to 12 grams per day divided into 4 equal doses every 6 hours, not to exceed a total of 12 grams per day.

In certain embodiments, azlocillin is typically administered to adults in doses of 8 to 18 grams per day, given in 4 to 6 equally divided doses.

In further embodiments, carbenicillin is administered to adults in doses of 30 to 40 grams per day, given by continuous infusion or in 4 to 6 equally divided doses. Daily doses of up to 600 mg/kg have been used to treat children with life-threatening infections.

Mezlocillin is administered in some embodiments to adults in doses of 100 to 300 mg/kg per day, given in 4 to 6 equally divided doses. The usual dose is 16 to 18 grams per day; for life threatening infections, 350 mg/kg per day may be administered, but in doses not to exceed 24 grams per day given in 6 equally divided doses every 4 hours. For children, the dose of mezlocillin is 150 to 300 mg/kg per day.

Nafcillin is in some embodiments intravenously administered to adults in doses of 3 grams per day, given in 6 equally divided doses every 4 hours, with doubled doses for very severe infections. In conventional administration, it is effective largely against gram-positive organisms. In children, a dose in additional embodiments is 20 to 50 mg/kg per day, in 2 equally divided doses every 12 hours. The oral dose for nafcillin in some embodiments ranges from 1 gram per day to 6 grams per day in 4 to 6 divided doses.

Oxacillin is administered in certain embodiments to adults in doses of 2 to 12 grams per day, in 4 to 6 equally divided doses. In conventional administration, it is effective largely against gram-positive organisms. In children, oxacillin is administered in doses of 100 to 300 mg/kg per day.

Piperacillin is administered to adults in doses ranging from 100 mg/kg, or 6 grams per day, in 2 to 4 equally divided doses, up to a maximum of 24 grams per day, in 4 to 6 equally divided doses. Higher doses have been used without serious adverse effects.

Ticarcillin is administered to adults in doses ranging from 4 grams per day to 18 grams per day administered in 4 to 6 equally divided doses. The usual dose is 200 to 300 mg/kg per day. For children, a typical dose of ticarcillin ranges from 50 mg/kg per day to 300 mg/kg per day, given in 3, 4 or 6 equally divided doses. The combination ticarcillin/clavulanate is administered to adults in doses of 200 to 300 mg/kg per day (based on ticarcillin content), in 4 to 6 equally divided doses. For adults, the usual dose is 3.1 grams (which contains 3 grams of ticarcillin and 100 mg of clavulanic acid) every 4 to 6 hours. The combination is also available in a dose of 3.2 grams, which contains 3 grams of ticarcillin and 200 mg of clavulanic acid.

In additional embodiments, methods and compositions concern cefamandole that is administered to adults in doses ranging from 1.5 grams per day, given in 3 equally divided doses every 8 hours, to 12 grams per day for life-threatening infections, given in 6 equally divided doses every 4 hours. In children, cefamandole is typically administered in doses ranging from 50 to 150 mg/kg per day, in 3 to 6 equally divided doses, not to exceed a total of 12 grams per day.

Cefazolin is administered in some methods to adults in doses of 750 mg per day, given in 3 equally divided doses every 8 hours. In severe, life-threatening infections, it may be administered at doses of 6 grams per day divided into 4 equal doses every 6 hours; in rare instances, up to 12 grams per day have been used. In children, the dose of cefazolin is 20 to 50 mg/kg per day, divided into 3 or 4 equal doses, with 100 mg/kg per day administered for severe infections.

In further embodiments, methods and compositions concern cefonicid that is administered to adults in doses ranging from 500 mg once daily, to 2 grams once daily for life-threatening infections. For intramuscular administration, a 2 gram dose should be divided into two 1-gram injections.

In some methods, cefoperazone is administered to adults in doses ranging from 2 grams per day, given in 2 equally divided doses every 12 hours, to 12 grams per day for severe infections, given in 2, 3 or 4 equally divided doses. Doses up to 16 grams per day have been administered without complications.

In certain embodiments, methods and compositions concern cefotetan that is administered to adults in doses of 1 to 4 grams per day, in 2 equally divided doses every 12 hours. Cefotetan may be administered in higher doses for life-threatening infections, not to exceed a total dose of 6 grams per day.

Cefotaxime is administered in certain embodiments to adults in doses ranging from 1 to 12 grams per day, not to exceed 12 grams per day (2 grams every 4 hours) for life-threatening infections. In children, the parenteral dose of cefotaxime is 50 to 180 mg/kg, divided into 4 to 6 equal doses.

In other embodiments, cefoxitin is administered to adults in doses ranging from 3 to 12 grams per day, given in 3, 4, or 6 equally divided doses. In children, cefoxitin is administered in doses of 80 to 160 mg/kg per day, given in 4 or 6 equally divided doses, not to exceed a total dose of 12 grams per day.

In additional embodiments, methods and compositions concern ceftazidime, which is administered to adults in doses ranging from 500 mg per day, given in 2 to 3 equally divided doses (every 8 or 12 hours), up to a maximum of 6 grams per day. In children, ceftazidime is administered intravenously in doses of 30 to 50 mg/kg, to a maximum of 6 grams per day.

In some cases, ceftizoxime is administered in certain embodiments to adults in doses ranging from 1 gram per day, given in 2 equally divided doses every 12 hours, to 12 grams per day for life-threatening infections, given in 3 equally divided doses every 8 hours. The usual adult dose is 1 to 2 grams every 8 or 12 hours. For children, a parenteral dose is 50 mg/kg every 6 or 8 hours, for a total daily dose of 200 mg/kg in some embodiments.

Ceftriaxone is administered in additional embodiments parentally to adults in doses ranging from 1 to 2 grams per day, given in 2 equally divided doses every 12 hours. It may be given in higher doses, not to exceed a total of 4 grams per day. In children, the dose of ceftriaxone is 50 to 75 mg/kg per day, not to exceed 2 grams per day. Ceftriaxone may be administered in doses of 100 mg/kg per day, not to exceed 4 grams per day.

In further embodiments, cefuroxime is administered to adults in doses ranging from 2.25 to 4.5 grams per day, in 3 equally divided doses every 8 hours. For life-threatening infections, 6 grams per day may be administered in 4 equally divided doses every 6 hours, and for meningitis, 9 grams per day may be administered in 3 equally divided doses every 8 hours. For children, the dose of cefuroxime is 50 to 150 mg/kg per day in 3 to 4 equally divided doses, or 240 mg/kg per day.

Cephalexin is formulated for oral administration, and is sometimes administered orally to adults in doses ranging from 1 to 4 grams per day in 2 to 4 equally divided doses. For children, doses may be 20 to 50 mg/kg per day in divided doses, with doses being doubled for severe infections.

Cephalothin is usually administered to adults in doses of 8 to 12 grams per day.

Fosfomycin is administered either orally or parenterally. In an oral formulation it is given as a single 3-gram dose mixed in 3-4 ounces of water and may be given daily. It may also be administered intravenously or intramuscularly in doses ranging from 2 to 4 grams daily, or up to 16 grams daily in certain cases.

D-cycloserine is administered orally in children and adults in doses ranging from 10 to 15 milligrams per kilogram daily, usually 500-750 milligrams for adults.

Bacitracin is administered topically to adults every 3-4 hours for 5-7 days for treatment of superficial infections. It may also be administered to children and infants via intramuscular injection of 900-1000 international units per kilogram per day, usually in divided doses.

Vancomycin is typically administered to adults via intravascular injection in doses ranging from 30-45 milligrams per kilogram per day. This may be divided over 2-4 administrations daily. It may also be dosed in larger loading doses of 25-30 milligrams per kilogram. It may further be administered orally in doses ranging from 500 milligrams up to 2 grams daily. In children it may be administered intravascularly in doses ranging from 15-45 milligrams per kilogram per day and orally in doses of 40 milligrams per kilogram per day, often with a daily maximum of 2 grams.

Daptomycin is administered to adults intravascularly in doses ranging from 6-8 milligrams per kilogram per day.

The overall composition includes each of the antibiotics in a therapeutically effective amount, along with a second compound that may be referred to as an antibiotic potentiator. The specific amount(s) is dependent on the antibiotic and other compound that is used, the disease or infection to be treated, and the number of times of day that the composition is to be administered.

An antibiotic potentiator refers to a compound or substance that is used in conjunction with an antibiotic to treat or inhibit a bacterial infection, such as a staphylococcal infection. These compounds combine with an antibiotic to increase the inhibitory effect of the antibiotic on the bacteria. Embodiments include an antibiotic potentiator or other compound that increases the ability of the antibiotic to inhibit the growth of bacteria in an in vitro assay, such as an assay disclosed in Example 2 herein, by about, at least about, or at most about the following amounts compared to the antibiotic in the absence of the other compound: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 times, or any range derivable therein.

Embodiments concern a number of compounds that can be used in combination with an antibiotic such as, for example, oxacillin. For example, clomifene, gossypol, menadione, or pyrvinium, or a prodrug or salt thereof, may be used individually or collectively with one or more antibiotics in methods and compositions provided herein. In other embodiments, oleandomycin or norfloxacin, or a prodrug or salt thereof, may be used individually or collectively with one or more antibiotics in methods and compositions provided herein. In other embodiments, the compounds listed in tables 7, 8, and 11 may be used as potentiators of one or more antibiotics in methods and compositions provided herein. In still further embodiments, compounds according to general formulas I to V described below may be used individually or collectively with one or more antibiotics in methods and compositions provided herein.

In some embodiments, the potentiator is a compound represented by general formula I:

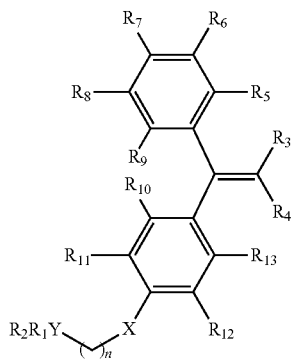

wherein X is methylene, NH, oxygen, sulfur, or carbonyl; n is an integer from 1 to 4; Y is CH or nitrogen; $R_1$ and $R_2$ are each independently hydrogen or alkyl; $R_3$ and $R_4$ are each independently hydrogen, halogen, alkyl, heterocycle, or aryl; $R_5$, $R_6$, $R_7$, $R_8$, and $R_9$ are each independently hydrogen, halogen, alkyl, haloalkyl, hydroxyl, alkoxy, thiol, thioether, amine, or alkylamine; $R_{10}$, $R_{11}$, $R_{12}$, and $R_{13}$ are each independently hydrogen, halogen, alkyl, haloalkyl, hydroxyl, alkoxy, thiol, thioether, amine, or alkylamine; or a tautomer or pharmaceutically acceptable salt thereof.

In certain instances, the potentiator according to general formula I is clomifene (2-(4-(2-chloro-1,2-diphenylethenyl)phenoxy)-N,N-diethyl-ethanamine), also known as clomiphene, clomifene citrate, and Clomifert (marketed as Clomid, Serophene, and Milophene), which is a selective estrogen receptor modulator (SERM) which promotes production of gonadotropins through inhibition of negative feedback on the hypothalamus. In certain circumstances, clomifene is used as ovulation inducer in treating female infertility. Additionally, clomifene has been used to treat male hypogonadism as an alternative to testosterone replacement therapy. While clomifene is now a generic drug, enclomiphene is its single isomer that is currently being developed under the brand name Androxal for use in men. In some embodiments, it is envisioned to administer clomifene or its isomers to a patient in a dose of up to 200 mg per day. In other embodiments it is envisioned to administer clomifene or its isomers to a patient in a dose of between 10 mg and 200 mg per day.

Clomifene Structure:

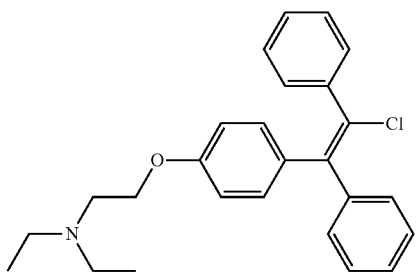 [SMILES: CCN(CC)CCOc1ccc(/C(=C(/Cl)c2ccccc2)c2ccccc2)cc1]

In some embodiments, the potentiator is a compound represented by general formula II:

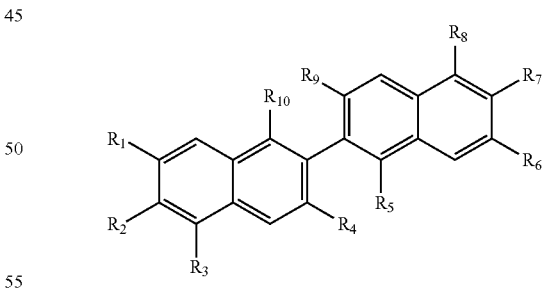

wherein $R_1$, $R_2$, $R_5$, $R_6$, $R_7$ and $R_{10}$ are each independently hydrogen, alkyl, halogen, hydroxyl, ether, alkoxy, acyl, thiol, thioether, amine, or alkylamine; and $R_3$, $R_4$, $R_8$ and $R_9$ are each independently hydrogen, alkyl, halogen, hydroxyl, ether, alkoxy, acyl, thiol, thioether, amine, or alkylamine; or a racemate, pharmaceutically acceptable salt, or tautomer thereof.

In certain instances, the potentiator according to general formula II is gossypol (2,2'-bis-(Formyl-1,6,7-trihydroxy-5-isopropyl-3-methylnaphthalene)), which is a natural phenolic aldehyde derived from the cotton plant. Gossypol acts as an inhibitor of several dehydrogenase enzymes and it has contraceptive properties in men and also acts as an antimalaria agent. It promotes apoptosis and is being investigated as a possible chemotherapy drug. Additionally, gossypol inhibits calcineurin, inhibits replication of the HIV-1 virus, causes low potassium levels, and is an effective protein kinase D inhibitor. In some embodiments it is envisioned to administer gossypol, or its related arylformaldehydes (damnacanthal and pyridoxal), to a patient in a dose of up to 50 mg per day. In other embodiments it is envisioned to administer gossypol, or its related arylformaldehydes, to a patient in a dose between 5 mg and 40 mg.

Gossypol Structure:

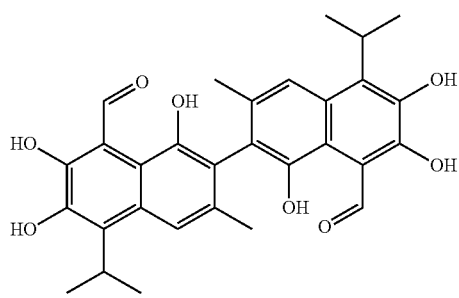 [SMILES: Cc1cc2c(C(C)C)c(O)c(O)c(C=O)c2c(O)c1-c1c(C)cc2c(C(C)C)c(O)c(O)c(C=O)c2c1O]

In some embodiments, the potentiator is a compound represented by general formula III:

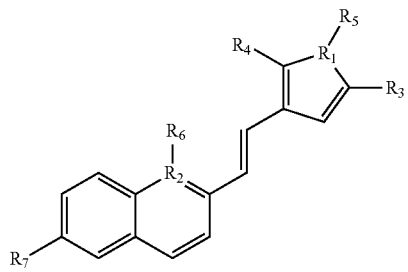

wherein $R_1$ is CH or N; $R_2$ is C or N; $R_3$ and $R_4$ are each independently hydrogen, alkyl, or halogen; $R_5$ is alkyl or aryl; $R_6$ is hydrogen or alkyl; and $R_7$ is hydrogen, alkyl, acyl, haloalkyl, halogen, heteroccle, amine, alkylamine, hydroxyl, alkoxy, ether, thiol, or thioether; or a racemate, pharmaceutically acceptable salt, tautomer, or geometric isomer thereof.

In certain instances, the potentiator according to general formula III is pyrvinium(2-[(E)-2-(2,5-Dimethyl-1-phenylpyrrol-3-yl)ethenyl]-N,N,1-trimethylquinolin-1-ium-6-amine), which is a compound with antithelmintic properties commonly used for treating enterobiasis (pinworms). Pyrvinium has also been shown to inhibit Wnt/beta-catenin pathway through stimulation of beta-catenin phosphorylation. In some embodiments it is envisioned to administer pyrvinium to a patient in a dose up to 6 mg per kg of body weight. In other embodiments it is envisioned to administer pyrvinium to a patient in a dose between 1 mg and 5 mg per kg of body weight.

Pyrvinium Structure:

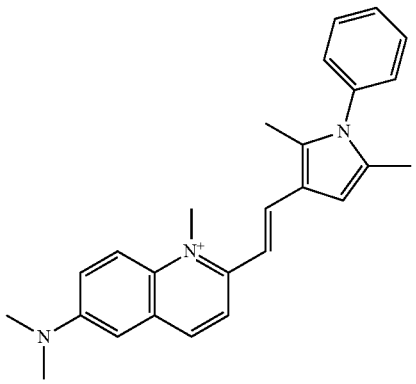

In some embodiments, the potentiator is a compound represented by general formula IV:

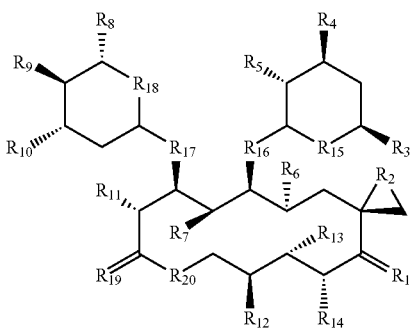

wherein $R_1$ is methylene or oxygen; $R_2$ is methylene, oxygen, or nitrogen; $R_3$, $R_4$, $R_5$, $R_6$, $R_7$, $R_8$, $R_9$, $R_{10}$, $R_{11}$, $R_{12}$, $R_{13}$ and $R_{14}$ are each independently hydrogen, alkyl, hydroxyl, alkoxy, amine, alkylamine, or halogen; $R_{15}$, $R_{16}$, $R_{17}$ and $R_{18}$ are each independently methylene, oxygen, carbonyl or NH; $R_{19}$ is methylene or oxygen; and $R_{20}$ is methylene, oxygen or NH.

In certain instances, the potentiator according to general formula IV is Oleandomycin, (3R,5R,6S,7R,8R,11R,12S,13R,14S,15S)-14-((2S,3R,4S,6R)-4-(dimethylamino)-3-hydroxy-6-methyltetrahydro-2H-pyran-2-yloxy)-6-hydroxy-12-((2R,4S,5S,6S)-5-hydroxy-4-methoxy-6-methyltetrahydro-2H-pyran-2-yloxy)-5,7,8,11,13,15-hexamethyl-1,9-dioxaspiro[2.13]hexadecane-4,10-dione, which is a natural 14membered-ring macrolide antibiotic, produced from strains of *Streptomyces antibioticus*. In some embodiments it is envisioned to administer oleandomycin, or its related ester triacetyloleandomycin to a patient in a dose of up to 2 g per day. In other embodiments it is envisioned to administer oleandomycin, or its related ester triacetyloleandomycin, to a patient in a dose between 0.1 g and 2 g.

Oleandomycin Structure:

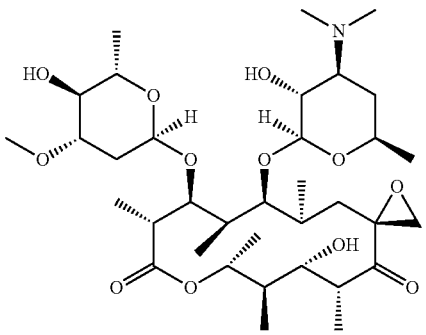 [SMILES: CO[C@H]1C[C@H](O[C@H]2[C@H](C)[C@@H](O[C@@H]3O[C@H](C)C[C@H](N(C)C)[C@H]3O)[C@@H](C)C[C@@]3(CO3)C(=O)[C@H](C)[C@@H](O)[C@@H](C)[C@@H](C)OC(=O)[C@@H]2C)O[C@@H](C)[C@@H]1O]

In some embodiments, the potentiator is a compound represented by general formula V:

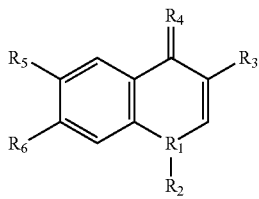

wherein $R_1$ is CH or N; $R_2$ is hydrogen, alkyl or acyl; $R_3$ is hydrogen, alkyl, alkoxy, haloalkyl, heterocycle, carboxylic acid, ester, or acyl; $R_4$ is methylene, oxygen, sulfur, or NH; $R_5$ is hydrogen, halogen, alkyl, hydroxyl, ether, alkoxy, acyl, thiol, thioether, amine, or alkylamine; and $R_6$ is hydrogen, alkyl, heterocycle, acyl, N-acyl, N-sulfonyl, amine, or alkylamine.

In certain instances, the potentiator according to general formula V is norfloxacin, 1-ethyl-6-fluoro-4-oxo-7-piperazin-1-yl-1H-quinoline-3-carboxylic acid, which is a first generation synthetic fluoroquinolone (quinolone) chemotherapeutic antibacterial agent. Norfloxacin is sometimes used to treat urinary tract infections. In some embodiments it is envisioned to administer norfloxacin to a patient in a dose of up to 2 g per day. In other embodiments it is envisioned to administer norfloxacin to a patient in a dose between 0.1 g and 0.7 g. In further embodiments, it is envisioned to administer norfloxacin to a patient in a dose of up to 400 mg every 12 hours.

Norfloxacin Structure:

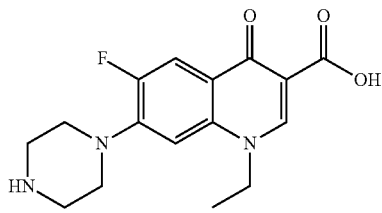 [SMILES: CCn1cc(C(=O)O)c(=O)c2cc(F)c(N3CCNCC3)cc21]

Menadione (2-Methylnaphthalene-1,4-dione), also known as menaphthone, Vitamin K3, beta-Methyl-1,4-naphthoquinone, 2-Methyl-1,4-naphthodione, and 2-Methyl-1,4-naphthoquinone, is a synthetic chemical compound with vitamin K activity, and it is often referred to as a provitamin. Menadione has been used experimentally as a chemotherapeutic agent, most recently in prostate cancer, and as a micronutrient for livestock and pets. In some embodiments it is envisioned to administer menadione, or its related analogs, to a patient in a dose of up to 100 mg per kg of body weight. In other embodiments it is envisioned to administer menadione, or its related analogs, to a patient in a dose between 0.1 mg and 50 mg per kg of body weight.

Menadione Structure:

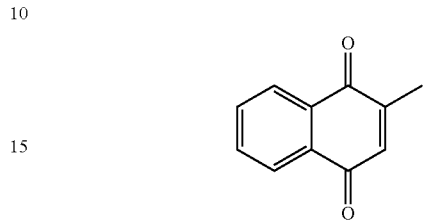

III. Dosages, Formulations, and Modes of Administration

A variety of methods and compositions are contemplated for inhibiting, preventing, or treating a bacterial infection using one or more antibiotics in combination with an antibiotic potentiator, such as one that inhibits or interferes with expression of the vraSR operon. In particular embodiments, the potentiator is a small molecule compound. Compositions that can be used to inhibit or treat a bacterial infection such as a staphylococcal infection may include one or more of the following substances: a first antibiotic, an antibiotic potentiator, a second antibiotic, a bacterial vaccine, an adjuvant, or a combination thereof. It is contemplated that a solution or composition may have additional components as well, which themselves may or may not be active ingredients. In some embodiments, a composition contains about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or mg/ml or μg/ml of a substance identified above, or a combination of substances or components, or any range derivable therein.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/kg or micrograms/kg/minute or mg/kg/min or micrograms/kg/hour or mg/kg/hour, or any range derivable therein, of a compound, such as a first antibiotic, an antibiotic potentiator, a second antibiotic, a bacterial vaccine, an adjuvant, or a combination thereof. Additionally, a subject may be administered a solution or composition that is described in the previous paragraph.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/kg or micrograms/kg/minute or mg/kg/min or micrograms/kg/hour or mg/kg/hour, or any range derivable therein, of oxacillin or vancomycin.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced. Moreover, a dose of one compound such as the antibiotic may be delivered prior to, concurrently with, and/or after an antibiotic potentiator. In certain embodiments where the first antibiotic, an antibiotic potentiator, a second antibiotic, a bacterial vaccine, and/or an adjuvant are administered with respect to at least one dose separately and/or at different times to a subject the intervening time between is or is about 10, 20, 30, 40, 50, minutes (or any range derivable therein) and/or 1, 2, 3, 4, 5, 6, 7, 8, 9, 10, 11, 12 hours (or any range derivable therein) or 1, 2, 3, 4, or 5 days (or any range derivable therein). In certain embodiments, an antibiotic is given with or before the antibiotic potentiator, such as about or up to about or at most about 1, 2, 3, 4, 5, 6, 7, 8, 9, 10, 15, 20, 25, 30, 35, 40, 45, 50, 55, 60, 70, 80, 90, 100, 110, 120, 130, 140, 150, 160, 170, or 180 minutes (or any range derivable therein) before the antibiotic potentiator.

A dose of oxacillin or vancomycin may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose of oxacillin or vancomycin may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced. Moreover, a dose of oxacillin or vancomycin may be delivered prior to, concurrently with, and/or after an antibiotic potentiator. In certain embodiments where the first antibiotic, an antibiotic potentiator, a second antibiotic, a bacterial vaccine, and/or an adjuvant are administered with respect to at least one dose separately and/or at different times to a subject the intervening time between is or is about 10, 20, 30, 40, 50, minutes (or any range derivable therein) and/or 1, 2, 3, 4, 5, 6, 7, 8, 9, 10, 11, 12 hours (or any range derivable therein) or 1, 2, 3, 4, or 5 days (or any range derivable therein). In certain embodiments, oxacillin or vancomycin is given with or before the antibiotic potentiator, such as about or up to about or at most about 1, 2, 3, 4, 5, 6, 7, 8, 9, 10, 15, 20, 25, 30, 35, 40, 45, 50, 55, 60, 70, 80, 90, 100, 110, 120, 130, 140, 150, 160, 170, or 180 minutes (or any range derivable therein) before the antibiotic potentiator.

An antibiotic may be administered for example, by any one of the following routes of administration: parenteral, intravenously, topically, intraocular, intranasal, rectal, vaginal, subcutaneous, intramuscular, arterial, sublingual, transmucosal, transdermal, or oral administration.

The antibiotic compositions may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In an embodiment, the antibiotic product is formulated in a manner such that it is suitable for oral administration.

For example, in formulating the antibiotic product for topical administration, such as by application to the skin, the at least two different dosage forms, each of which contains an antibiotic, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the embodiments to provide an antibiotic product in the form of a patch, which includes antibiotic dosage forms having different release profiles, as hereinabove described.

In addition, the antibiotic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antibiotic with different release profiles may be formulated for rectal or vaginal administration, as known in the art. This may take the form of a cream or emulsion, or other dissolvable dosage form similar to those used for topical administration.

As a further embodiment, the antibiotic product may be formulated for use in inhalation therapy by coating the particles and micronizing the particles for inhalation.

In some embodiments, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is an immediate release tablet, and may also include two or more additional tablets, each of which provides for a delayed release of the antibiotic.

The formulation of an antibiotic product including at least three dosage forms with different release profiles for different routes of administration is deemed to be within the skill of the art from the teachings herein. As known in the art, with respect to delayed release, the time of release can be controlled by the concentration of antibiotics in the coating and/or the thickness of the coating.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons. It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Piuronic line of surfactants, or any other material with surface active properties, or any combination of the above. These materials may be present in the rate of 0.05-15% (W/W).

In certain embodiments there is a delayed release component. The components in this composition are the same immediate release unit, but with additional polymers integrated into the composition, or as coatings over the pellet or granule.

Materials that can be used to obtain a delay in release suitable for this component of the embodiment can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5-25% (W/W) of this component.

As an enteric release composition the components are the same as the immediate release component, but with additional polymers integrated into the composition, or as coatings over the pellet or granule.

The kind of materials useful for this purpose can be, but are not limited to, cellulose acetate phthalate, Eudragit L, and other phthalate salts of cellulose derivatives. These materials can be present in concentrations from 4-20% (W/W).

Pharmaceutical Compositions and Kits

Suitable preparations, e.g., substantially pure preparations of the agents described herein may be combined with pharmaceutically acceptable carriers, diluents, solvents, excipients, etc., to produce an appropriate pharmaceutical composition. The embodiment therefore provides a variety of pharmaceutically acceptable compositions for administration to a subject comprising (i) an antibiotic potentiating agent; and (ii) a pharmaceutically acceptable carrier or excipient. The embodiment further provides a pharmaceutically acceptable composition comprising (i) an antibiotic potentiating agent; (ii) an antibiotic whose activity is potentiated by the compound; and (iii) a pharmaceutically acceptable carrier or excipient. The embodiment further provides a pharmaceutically acceptable unit dosage form containing a predetermined amount of an antibiotic and a predetermined amount of an antibiotic potentiating agent, wherein the predetermined amounts are selected so that the antibiotic potentiating agent potentiates the antibiotic when the unit dosage form is administered to a subject.

Further provided are pharmaceutically acceptable compositions comprising a pharmaceutically acceptable derivative (e.g., a prodrug) of any of the potentiating agents of the embodiments, by which is meant any non-toxic salt, ester, salt of an ester or other derivative of a potentiating agent, upon administration to a recipient, is capable of providing, either directly or indirectly, the potentiating agent. A wide variety of appropriate pharmaceutically acceptable salts are well known in the art. For example, S. M. Berge et al., describe pharmaceutically acceptable salts in detail in J. Pharmaceutical Sciences, 66:1, 1977, incorporated herein by reference. Pharmaceutically acceptable salts of the compounds of this embodiment include those derived from suitable inorganic and organic acids and bases.

The term "pharmaceutically acceptable carrier, excipient, or vehicle" refers to a non-toxic carrier, excipient, or vehicle that does not destroy the pharmacological activity of the agent with which it is formulated. Pharmaceutically acceptable carriers, excipients, or vehicles that may be used in the compositions of this embodiment include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

Pharmaceutically acceptable salts of the agents of this embodiment include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the embodiment and their pharmaceutically acceptable acid addition salts.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In all cases, the composition should be sterile, if possible, and should be fluid to the extent that easy syringability exists.

Pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol or sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present embodiment also contemplates delivery of compositions using a nasal spray.

For topical applications, the pharmaceutically acceptable compositions may be formulated in a suitable ointment containing the active component suspended or dissolved in one or more carriers. Carriers for topical administration of the compounds of this embodiment include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For local delivery to the eye, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments. It will be appreciated that a range of different dosage combinations (i.e., doses of the antibiotic and antibiotic potentiating agent) can be used.

Exemplary doses include milligram or microgram amounts of the inventive compounds per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) For local administration (e.g., intranasal), doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

The presented embodiments also include pharmaceutical packs or kits comprising one or more containers (e.g., vials, ampoules, test tubes, flasks, or bottles) containing one or more ingredients of the inventive pharmaceutical compositions, for example, allowing for the simultaneous or sequential administration of the antibiotic potentiating agent and antibiotic agent(s) it potentiates. Optionally associated with such container(s) can be a notice in the form prescribed by a governmental agency regulating the manufacture, use or sale of pharmaceutical products, which notice reflects approval by the agency of manufacture, use or sale for human administration. Different ingredients may be supplied in solid (e.g., lyophilized) or liquid form. Each ingredient will generally be suitable as aliquoted in its respective container or provided in a concentrated form. Kits may also include media for the reconstitution of lyophilized ingredients. The individual containers of the kit are preferably maintained in close confinement for commercial sale.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Examples of pharmaceutically acceptable salts derived from appropriate bases include alkali metal, alkaline earth metal, ammonium and N+(C1-4 alkyl)4 salts.

Representative pharmaceutically acceptable alkali or alkaline earth metal salts include sodium, lithium, potassium, calcium, magnesium, and the like.

Further pharmaceutically acceptable salts include, when appropriate, nontoxic ammonium, quaternary ammonium, and amine cations, for example formed using counterions such as halide, hydroxide, carboxylate, sulfate, phosphate, nitrate, lower alkyl sulfonate and aryl sulfonate.

Physiologically acceptable carrier or excipient: As used herein, the term "physiologically acceptable carrier or excipient" refers to a carrier medium or excipient which does not interfere with the effectiveness of the biological activity of the active ingredients and which is not excessively toxic to the host at the concentrations at which it is administered. The term includes solvents, dispersion media, coatings, antibacterial and antifungal agents, isotonic agents, absorption delaying agents, and the like. The use of such media and agents for the formulation of pharmaceutically active substances is well-known in the art (see, for example, "Remington's Pharmaceutical Sciences", E. W. Martin, 18th Ed., 1990, Mack Publishing Co.: Easton, Pa., which is incorporated herein by reference in its entirety).

IV. Examples

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Test Strain Construction—The test strain (923) is a USA300 MRSA clinical isolate for which the dependence of Mc resistance on vraSR has been well characterized (1, 2). To produce a reporter for vra operon transcription, the vra promoter ($P_{vra}$) was PCR amplified from strain 923 using primers $P_{vra}$-F (5'-aaagaattctgaaggtatggtattagctattg-3' (SEQ ID NO:1)) and ($P_{vra}$-R) (5'-aaa ggatccgttgatgtcgatgatatgtttg-3'(SEQ ID NO: 2)) containing EcoRI and BamHI restriction sites (underlined) and inserted into pXen-1 (Caliper Life Sciences) in the compatible restriction sites present upstream of the luxABCDE operon (lux) from *Photorhabdus luminescens*. This gene cluster (lux) produces all the components required for luminescence obviating the need for exogenous substrate (3). The ligation was transformed into *E coli* strain TOP10 (Invitrogen) and colonies were selected on ampicillin (100 μg/ml). The resulting plasmid was isolated and called pPvra::lux. With this construct, the $P_{vra}$ drives expression of the lux gene cluster. $pP_{vra}$::lux was transformed into the restriction negative intermediate *Staphylococcus aureus* host strain, RN4220 (Kreiswirth) and was then isolated from RN4220 and transformed into MRSA strain 923 (923 $pP_{vra}$-lux). The vra promoter and lux genes were confirmed as wild-type by Sanger sequence analysis. Strains containing $pP_{vra}$-lux were cultured in the presence of chloramphenicol (Cm) to maintain the plasmid.

Validation of Test Strain 923 $pP_{vra}$::lux The optimal concentration of oxacillin for vra induction and luminescence was chosen by preliminary testing of a range of oxacillin concentrations (FIG. 1). Briefly, a saturated overnight culture of the test strain (923 $pP_{vra}$-lux) in TSB (containing 10 μg/ml chloramphenicol for plasmid selection) was diluted 1:100 into fresh TSB containing 0 to 6 μg/mL of oxacillin. A 100 μL cell plus oxacillin suspension was applied to each well of a white plastic clear-bottomed 96-well plate (Costar) and the plate was incubated at 37° C. Absorbance at 600 nm and luminescence were monitored every 5 minutes for 24 hours using a microplate reader (Fluostar Optima, BMG).

Small-Molecule Screening—The Prestwick Chemical library was used for the small molecule library. The Prestwick Chemical Library contains approximately 1200 drugs with history of use in humans, with the greatest possible degree of "drug-likeliness". It was supplied in 384 well format in 10 mM concentration in DMSO and was re-plated to a 96 well daughter plates to a 1 mM concentration.

A saturated overnight culture of the test strain (923 pPvra-lux) in TSB (containing 10 μg/ml chloramphenicol for plasmid selection) was diluted 1:100 into fresh TSB. A 99 μL cell suspension and 1 μL test compound (final concentration 10 μM dissolved in DMSO,) was applied to a 96-well plate and incubated at 37° C. The OD at 530 nm and luminescence were recorded at intervals of 0, 1, 2, 3, 4, and 24 hours. All compounds were tested in the presence and absence of oxacillin (2 μg/mL). For each 96-well plate assayed, 80 compounds were tested. The remaining 16 wells contained either cells in TSB alone (7 replicates), cells with oxacillin (2 μg/mL, 7 replicates), or blank TSB (2 replicates). Due to instrument limitations, only half of the library was screened each day (7 plates, 560 compounds). The full library was screened twice. Compounds identified in the primary screen that satisfied the criteria described in Example 2 were subjected to secondary screening.

In the secondary screen each microtiter plate contained either cells in TSB alone (16 replicates), cells with oxacillin (2 μg/mL, 31 replicates), or cells with test compound and oxacillin (2 μg/mL, 49 wells). Each compound was assayed in four separate biological replicates.

Confirmation of vraR Inhibition Via qRT-PCR—A saturated overnight culture of strain 923 was diluted 1:100 into fresh TSB and grown at 37° C. with shaking After one hour, test compound (10 μM) and oxacillin (2 μg/mL) were added and the culture was incubated for an additional hour. Bacteria were lysed via lysostaphin incubation (Ambi, 200 µg/mL) for 10 minutes at 25° C. RNA was purified with the Qiagen RNeasy kit, including treatment with DNase and cDNA generated using the high-capacity cDNA Archive Kit (Applied Biosystems). qRT-PCR was performed using molecular beacons and primers obtained from IDT. Specifically, a multiplex reaction consisting of a vraR probe (PrimeTime Probe/5' 6-FAM/TTG CCA AAG/ZEN/CCC ATG AGT TGA AGC CA/3'IABkFQ/) (SEQ ID NO: 3) with primers vraR-R (5'-TAG TTG GTG AAG GCG CTT CTG GTA-3') (SEQ ID NO: 4) and vraR-F (5'-TCG TCG CTT CTA CAC CAT CCA TGT-3') (SEQ ID NO: 5) to detect vra operon transcription combined with a gyrB endogenous control probe (/5Cy5/AAA TGG GAC GTC CAG CTG TCG AAG TT/3IAbRQSp/) (SEQ ID NO: 6) with primers (gyrBR 5'-CCG CCA AAT TTA CCA CCA GCA TGT-3') (SEQ ID NO: 7) and (gyrBF 5'-AAC GGA CGT GGT ATC CCA GTT GAT-3') (SEQ ID NO: 8). Relative Quantification was performed using the ΔΔCT method facilitated by using the ABI Prism 7300 Sequence Detection Software (version 1.2.3) (4) (Applied Biosystems). Strain 923 grown in the absence of oxacillin was used as the comparator condition unless the oxacillin induced condition is indicated (5).

Example 2

Assay Strategy

Assay Development for Screening of Inhibitors of Growth and vraSR Expression—By coupling the vraSR promoter to the luxABCDE operon, we were able to simultaneously monitor cell growth as a function of optical density (OD) and PvraSR expression as a function of luminescence (lux) (measured in relative light units (LU)). Prior to screening the Prestwick compound library for inhibitors of growth and/or luminescence, the optimal concentration of oxacillin and time points for collection of $OD_{600}$ and LUs, and criteria for classifying a compound. To this end, cells were cultured in 96 well microtiter plates, and growth and luminescence monitored in a plate reader.

When using CLSI guidelines, strain 923 has a 24-h oxacillin MIC of 16-32 µg/mL (Boyle-Vavra et al). However, when cultured in the 96-well format, the MIC of oxacillin of strain 923 was 8 µg/mL, and in 923 containing pPvra-lux, the MIC of oxacillin further dropped to 5 µg/mL (FIG. 1A). Based on the MIC of oxacillin obtained in the 96-well format, we measured the OD600 and LU of cultures of strain 923 Pvra-lux supplemented with oxacillin in concentrations spanning 0 to 6 mg/L (FIG. 1). We found that vraSR expression reached its maximum 2 hours after induction (FIG. 1B), and 2 µg/mL oxacillin was the minimum concentration sufficient for maximal vraSR expression (FIG. 1C). Therefore, the library was screened using 2 µg/ml oxacillin, luminescence was the recorded at 2 hours, and $OD_{600}$ recorded at 24 hrs.

Figure 2:
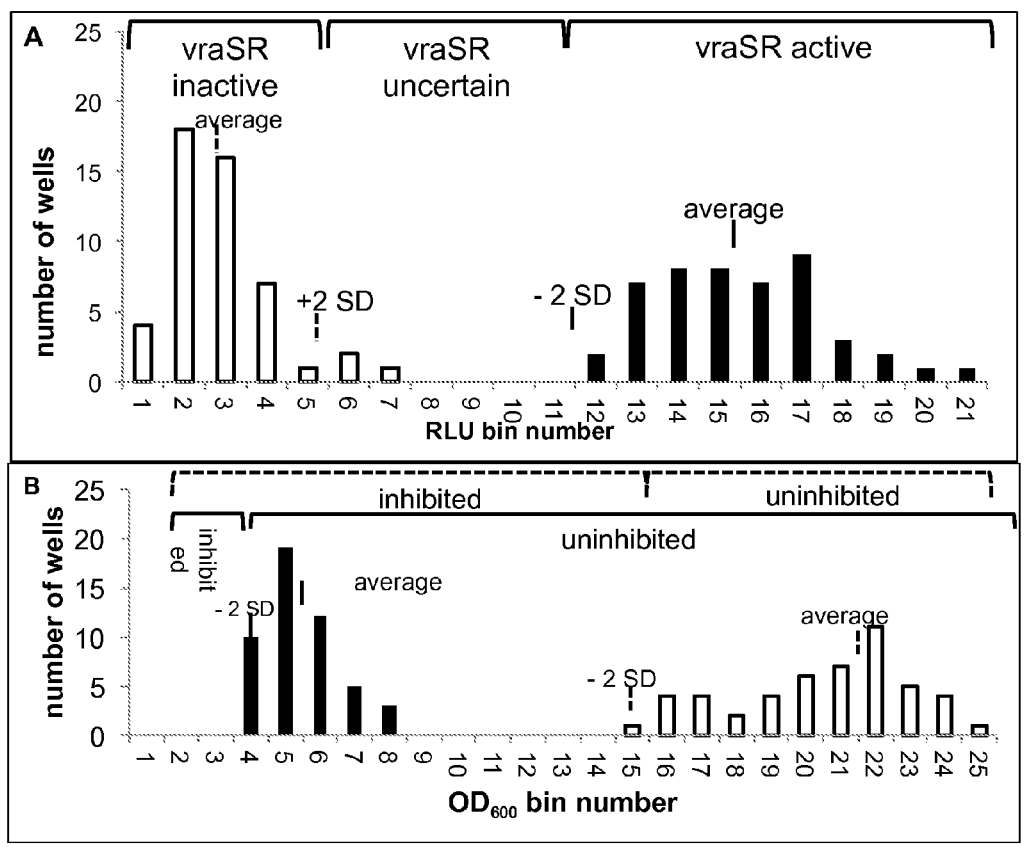
FIG. 2A-B: Distribution of OD and LU. Criteria for classification of growth and luminescence inhibition are based on reference data of strain 923 pPvra-lux grown in the presence or absence of oxacillin (2 μg/mL) (+/−Ox). (A) luminescence (B) absorbance. solid bars=oxacillin added (+Ox), empty bars=no oxacillin (−Ox).

To define the LU and $OD_{600}$ cutoff values for defining inhibition of luminescence and growth, respectively, data was obtained from 49 wells seeded with cell culture supplemented with 2 µg/ml oxacillin and 49 control wells seeded with cultures lacking oxacillin. The values were partitioned into bins for ease of visualization. The data were normally distributed for both LU (FIG. 2A) and OD600 values (FIG. 2B). Cutoff values were set at 2 SDs above or below the mean.

Values were classified as either vraSR-inactive, (RLUs less than two SDs above the mean of the no-oxacillin controls (FIG. 2A, white bars), vraSR-active (any value less than two SDs below the mean LU of the oxacillin-induced wells (FIG. 2A, black filled bars), or vraSR-uncertain (any value which falls between the other two categories).

For judging cell growth, cultures were classified as either "uninhibited" or "inhibited". "Uninhibited" was defined as any value less than 2 SDs below the mean of the no-oxacillin cultures (white bars), while "inhibited" wells had any value <2 SDs below the mean of the no oxacillin cultures (black bars, bins 4-8)(FIG. 2B).

Primary Screen—The Prestwick Chemical Library was screened twice for its effects on growth and vraSR induction of the test strain, both in the presence and absence of oxacillin. First, the compounds were stratified into three categories by their effects on growth of MRSA strain 923 as follows: (a) "Primary Screen Potentiators" (b) "Primary Screen Growth Inhibitors", or (c) "growth noninhibiting". Compounds that were growth "inhibitors" in one duplicate and growth "noninhibitors" in the other were classified as "inhibitors".

Of the 112 Primary Screen Potentiators 6) twenty-one are known antibiotics. Also included are antimicrobials that are used to treat non-bacterial infections (specifically called antibiotics). These include antiviral, antiprotozoal, antihelmentic, antifungal, and antimalarial agents (including the last resort agent artemisinin) The remaining Primary Screen Potentiators have not previously been known to be antimicrobial. The Primary Screen Potentiators were further categorized as "vraSR neutral" (N=65), "vraSR stimulators" (N=5), or "vraSR repressors" (N=42) (Table 8). Compounds that were "vraSR neutral" in one screen but "vraSR repressors" or "vraSR stimulators" in the other were classified as "vraSR repressors" or "vraSR stimulators", respectively.

The Primary Screen Growth Inhibitors (Tables 9 and 10) included previously known antibacterial, antifungal, antihelmenthic, antiparasitic, antiviral, and antiseptic agents. The Primary Screen Growth Inhibitors further includes compounds with other known medical uses including an anti-angina agent, an anticoagulant, an antidepressant, and a cholesterol reducer.

Secondary Screen: All compounds classified in the primary screen as synergists that were vraSR-stimulating or -repressing (as shown in Table 8) were screened in a secondary assay for their effects on both growth and $P_{vra}$:: lux induction by oxacillin. Also included in the secondary screen were two compounds that were not known to be antibiotics but were shown in the primary assay to be strong growth inhibitors on their own and repressed $P_{vra}$::lux in both primary screens (gossypol and pyrvinium). Each compound was tested four separate times at 10 µM in the presence of oxacillin (2 µg/mL) and luminescence was measured every 15 minutes. Relative growth (RG) and relative luminescence (RL) was calculated as the ratio between the $OD_{600}$ or max LU value in the presence of compound and oxacillin over the average from pooled control values obtained from the same plate. The average LU of the pooled positive controls from all runs in the secondary assay (grown in the presence of oxacillin) was 144 (SD+/−16) compared with 53 LU in the absence of oxacillin (SD+/−8), demonstrating that the oxacillin induced $P_{vra}$::lux by 2.7 fold. Compounds that produced an average RG (ratio of the $OD_{600}$ of the culture grown with test compound combined with oxacillin to that of oxacillin alone) of <0.8 were classified as oxacillin synergists or potentiators. The relative luminescence (RL) was the ratio of the LU produced in the presence of the test compound combined with oxacillin to that produced by oxacillin alone.

Compounds were classified as "vraSR repressors" (mean RL of <0.8), "vraSR stimulators", (mean RL>1.2), and "vraSR neutral" (mean RL between 0.80-1.2). As expected, the growth "noninhibitors" were primarily vraSR "neutral", while the growth "inhibitors" were primarily vraSR "repressors." As shown in Table 1, 15 of the 49 compounds screened in the secondary assay potentiated oxacillin ("inhibited" in the $OD_{600}$ category). In contrast, 34 compounds had no effect on growth in the presence of oxacillin ("un" in the $OD_{600}$ category). Among the oxacillin potentiators, there were 2 vraSR stimulators, 3 vraSR neutral compounds and 10 vraSR repressors.

TABLE 1

Secondary Screen: Relative growth (RG) and Relative luminescence (RL) produced by MRSA strain USA300 $P_{vra}$-lux in the presence of compounds and oxacillin. Uninhibited (un), neutral (N).

| Chemical name | RG avg | RL avg | $OD_{600}$ category | Effect on vraSR transcription |
|---|---|---|---|---|
| Gossypol | 0.16 | 0.11 | inhibited | repress |
| Oleandomycin phosphate | 0.19 | 0.20 | inhibited | repress |
| Pyrvinium pamoate | 0.39 | 0.31 | inhibited | repress |
| Norfloxacin | 0.40 | 0.33 | inhibited | repress |
| Diethylstilbestrol | 0.41 | 0.26 | inhibited | repress |
| Spiramycin | 0.43 | 0.31 | inhibited | repress |
| Cephalothin sodium salt | 0.45 | 0.36 | inhibited | neutral |
| Lynestrenol | 0.47 | 0.26 | inhibited | repress |
| Fluspirilen | 0.47 | 0.28 | inhibited | stimulate |
| Cefotiam hydrochloride | 0.64 | 0.64 | inhibited | neutral |
| Clomiphene citrate (Z,E) | 0.68 | 0.39 | inhibited | repress |
| Menadione | 0.69 | 0.47 | inhibited | repress |
| Ursolic acid | 0.77 | 0.71 | inhibited | repress |
| Sanguinarine | 0.78 | 0.47 | inhibited | repress |
| Cefoperazone dihydrate | 0.79 | 0.77 | inhibited | neutral |
| Amiodarone hydrochloride | 0.84 | 0.68 | inhibited | stimulate |
| Betulinic acid | 0.87 | 0.83 | un | neutral |
| Guanfacine hydrochloride | 0.88 | 0.79 | un | neutral |
| Doxorubicin hydrochloride | 0.88 | 0.83 | un | repress |
| Liothyronine | 0.88 | 0.87 | un | neutral |
| Spectinomycin dihydrochloride | 0.89 | 0.77 | un | neutral |
| Acacetin | 0.91 | 0.88 | un | neutral |
| Azlocillin sodium salt | 0.91 | 0.78 | un | neutral |
| Domperidone | 0.91 | 0.85 | un | neutral |
| Mitoxantrone dihydrochloride | 0.94 | 0.83 | un | neutral |
| Phenethicillin potassium salt | 0.94 | 0.88 | un | neutral |
| Ethynylestradiol 3-methyl ether | 0.95 | 0.97 | un | repress |
| Beclomethasone dipropionate | 0.96 | 0.96 | un | neutral |
| Calciferol | 0.96 | 0.88 | un | neutral |
| Raloxifene hydrochloride | 0.97 | 0.85 | un | neutral |
| Clidinium bromide | 0.97 | 0.95 | un | neutral |
| Nifurtimox | 0.97 | 0.95 | un | repress |
| Cinnarizine | 0.97 | 0.94 | un | neutral |
| Indoprofen | 0.98 | 0.87 | un | neutral |
| Daunorubicin hydrochloride | 0.98 | 1.00 | un | repress |
| Sulfamerazine | 0.99 | 1.01 | un | neutral |
| Furaltadone hydrochloride | 1.00 | 1.01 | un | repress |
| Nystatine | 1.00 | 1.04 | un | neutral |
| Digitoxigenin | 1.01 | 0.97 | un | neutral |
| Benzthiazide | 1.01 | 0.95 | un | neutral |
| Bucladesine sodium salt | 1.02 | 0.94 | un | neutral |
| Droperidol | 1.02 | 0.91 | un | neutral |
| Butacaine | 1.03 | 0.98 | un | neutral |
| Oxalamine citrate salt | 1.03 | 1.00 | un | neutral |
| Trimeprazine tartrate | 1.04 | 0.96 | un | neutral |
| Cinoxacin | 1.05 | 1.03 | un | neutral |
| Meclofenoxate hydrochloride | 1.08 | 1.08 | un | neutral |
| Promazine hydrochloride | 1.09 | 1.08 | un | neutral |
| Trichlormethiazide | 1.10 | 1.06 | un | neutral |

Figure 3:
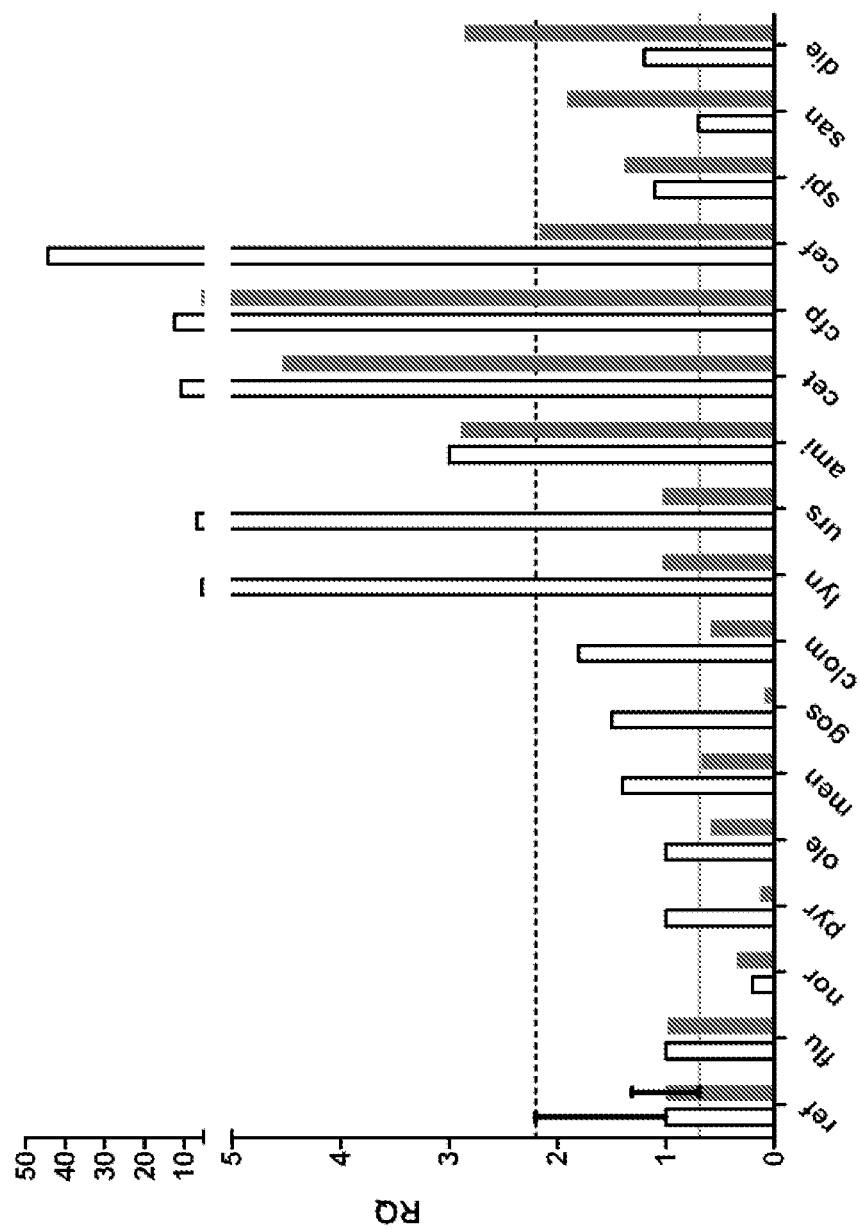
FIG. 3: Relative Quantification RT-PCR of vraR in the presence of test compounds, with and without oxacillin. Relative quantities (RQ) of vraR transcription were calculated with the reference sample containing no compound without oxacillin (ref, white bars) or oxacillin alone (ref, Dark bars). Open bars show test compound alone, solid bars show test compound plus oxacillin. Cut-offs for vraSR stimulation and repression are one SD over or under reference (shown in reference error bars).
Figure 4:
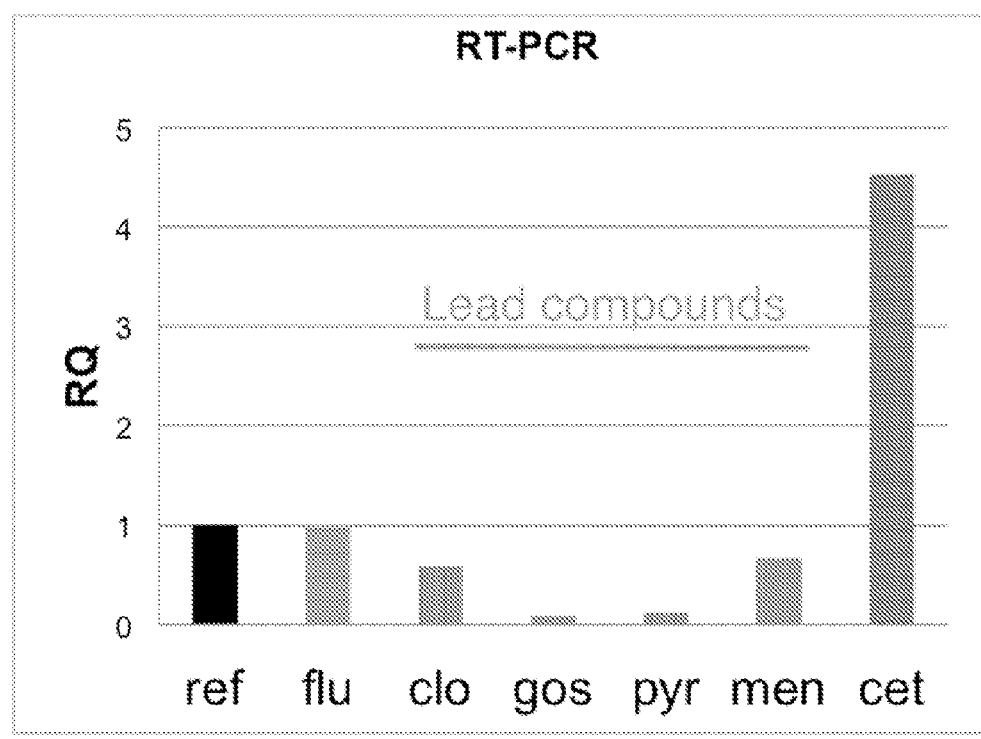
FIG. 4: Lead compound details. Relative quantities of vraR transcription were calculated using the standard ΔΔCT method using strain 923 plus oxacillin alone as the reference (ref). Compounds were added to cells in mid-log and RNA was isolated 1 hour later using an RNA micro purification kit (Qiagen). cDNA was produced and used in RT-PCR with a FAM-labeled vraR probe (IDT) and a Cy5-labeled gyrB endogenous control probe (IDT) using a described protocol (1). Data were analyzed using the ABI Prism 7300 Sequence Detection Software (version 1.2.3). In the presence of oxacillin, fluspirilen (flu) was vraR neutral, cefotiam (Cet) was a vraR activator and clomifene (clo), menadione (men), gossypol (gos) and pyrvinium (pyr) were vraR inhibitors.
Figure 5:
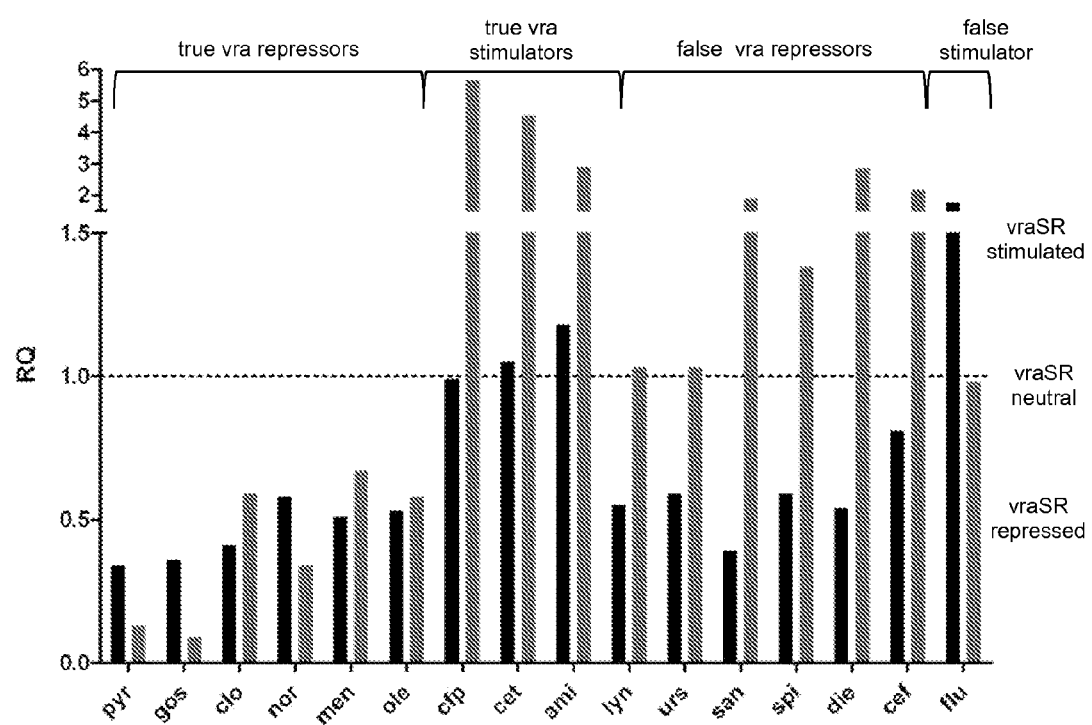
FIG. 5: Validation of luminescence as a reporter for vraSR activity by RT-PCR. For luminescence, (black bars) the RQ of vraSR was calculated as the ratio of the LU from the test compound with oxacillin to oxacillin alone. For RT-PCR, RQ was calculated in the standard method with the reference sample containing no compound. Black bars show luminescence, grey bars show RT-PCR.

Tertiary Screen: RT-PCR—From the secondary screen, all growth inhibitors were passed on to the tertiary screen. The test compound's effects on vraR transcription in the presence (FIG. 3, solid bars) and absence (FIG. 3, open bars) of oxacillin was measured via RT-PCR. A sample grown without compound was used as a reference condition in the RQ calculation and by definition has an RQ=1. Induction of vraR by a compound in the absence of oxacillin was defined as any value >1 SD above the reference (FIG. 5, dotted line). Repression of oxacillin-stimulated vraR transcription was defined as any value >one SD below the reference (FIG. 3, solid line). FIG. 4 highlights those compounds deemed to be lead compounds.

Using these definitions, compounds were classified into 4 categories (Table 2). One compound had no effect on vraR transcription in the absence or presence of oxacillin. Six compounds had little effect on vraR on their own, but attenuated induction by oxacillin. An additional six compounds stimulated vraR transcription both in the absence and presence of oxacillin. The remaining three compounds had little effect on vraR on their own, but enhanced oxacillin's effect on vraR transcription (especially diethylstilbesterol).

TABLE 2

Growth inhibitors of MRSA strain 923 and their effect on vraSR transcription

| | Effect on vraSR Transcription | | |
|---|---|---|---|
| Inhibitor Compound (bold indicates non-antibiotic) | Compound alone | With oxacillin | Effect on vraSR transcription |
| fluspirilene | none | none | No effect |
| pyrvinium, oleandomycin, menadione, gossypol, clomifene norfloxacin | none or repress | repress | Little effect alone, blocks oxacillin's effect on vraSR |
| lynestranol, ursolic acid, amiodarone, cefotiam, cefoperazone, cephalothin | stimulate | none or super-stimulate | Stimulates alone, similar to cell-wall active antibiotics |
| spiramycin, sanguinarine, diethylstilbestrol | None | super-stimulate | No effect alone, enhances oxacillin's effect on vraSR |

Comparison of Secondary and Tertiary Screens—To evaluate the accuracy of the lux system as a reporter for vraSR expression, the RQ values in the presence of oxacillin were compared between the lux screen performed in the plate reader (FIG. 5, black bars) and the qRT-PCR screen (FIG. 5, grey bars). For nine compounds (56%), the qRT-PCR assay confirms the lux observations. These compounds were classified as "true" repressors or stimulators. gossypol (gos), pyrvinium pamoate (pyr), norfloxacin (nor), oleandomycin phosphate (ole), clomiphene citrate (clo) and menadione (men) repressed in all three screens and were treated subsequently as true vraSR expression repressors. An additional six compounds (38%) appeared to be repressors in the lux screen, but were neutral or stimulators via qRT-PCR, and were classified as "false repressors". One compound (fluconazole, flu) appeared to be a stimulator in the lux screen, but was neutral via qRT-PCR, and was classified as a "false stimulator".

Synergy Testing—Checkerboard MIC testing. The interactions of clomiphene, gossypol, pyrvinium and menadione with oxacillin were assessed for synergy by checkerboard MIC testing using each test compound (0.25 to 16 µg/mL) and oxacillin (2 to 32 µg/mL) in 2-fold serial dilutions according to the method in CLSI M07-A8. Oxacillin and compounds were prepared to 4 times their final concentration in TSB containing 2% NaCl. 250 µL of each concentration of oxacillin and each concentration of compound were applied to a 48-well plate to create a 6×8 checkerboard. A concentration series of oxacillin alone and compound alone were included so that the MIC of oxacillin and test compound alone could be determined. All wells were inoculated with 500 µL of a 1×10$^6$ cfu/mL suspension of strain 923 in TSB containing 2% NaCl. Plates were incubated overnight at 37° C. and MICs were visually determined at 24 h.

Tables 3a and 3b summarize the MICs of oxacillin obtained in the presence of various concentrations of each compound. The concentration of menadione was scaled to higher concentrations (Table 3b) based on a preliminary experiment. For each compound, the MIC of oxacillin decreased in the presence of the compound in a dose-dependent fashion. Conversely, the MIC of each compound was lowered by oxacillin (not shown). To assess true synergy between oxacillin and each compound, the Fractional Inhibitory Concentration (FIC) index was determined for those wells that corresponded to an MIC in the checkerboard. Using an FIC index <0.5 to define synergy (14), each of the 4 compounds met the definition of synergy in at least one well. The FIC index is a sum of the FIC of each drug used in the combination as follows:

$$\text{FIC index} = FIC_i = \frac{[Ox] \text{ in well}}{MIC \text{ of } Ox \text{ alone}} + \frac{[\text{compound}] \text{ in well}}{MIC \text{ of compound alone}}$$

TABLE 3(a)

| Compound | oxacillin MIC (mg/L) | | |
|---|---|---|---|
| (µM) | clo | Gos | pyrv |
| 0 | | | |
| 0.25 | 32 | 32 | 16 |
| 0.5 | 16 | 32 | 4 |
| 1 | 32 | 16 | 2 |
| 2 | 32 | 4 | 0 |

TABLE 3(a)-continued

| Compound | oxacillin MIC (mg/L) | | |
|---|---|---|---|
| (µM) | clo | Gos | pyrv |
| 4 | 8 | 2 | 0 |
| 8 | 8 | 2 | 0 |
| 16 | 2 | 2 | 0 |

TABLE 3(b)

| Men (µM) | oxacillin MIC (mg/L) |
|---|---|
| 0 | 32 |
| 10.8 | 16 |
| 12.3 | 16 |
| 14.1 | 16 |
| 16.1 | 2 |
| 18.4 | 2 |
| 21 | 2 |
| 24 | 2 |

Figure 6:
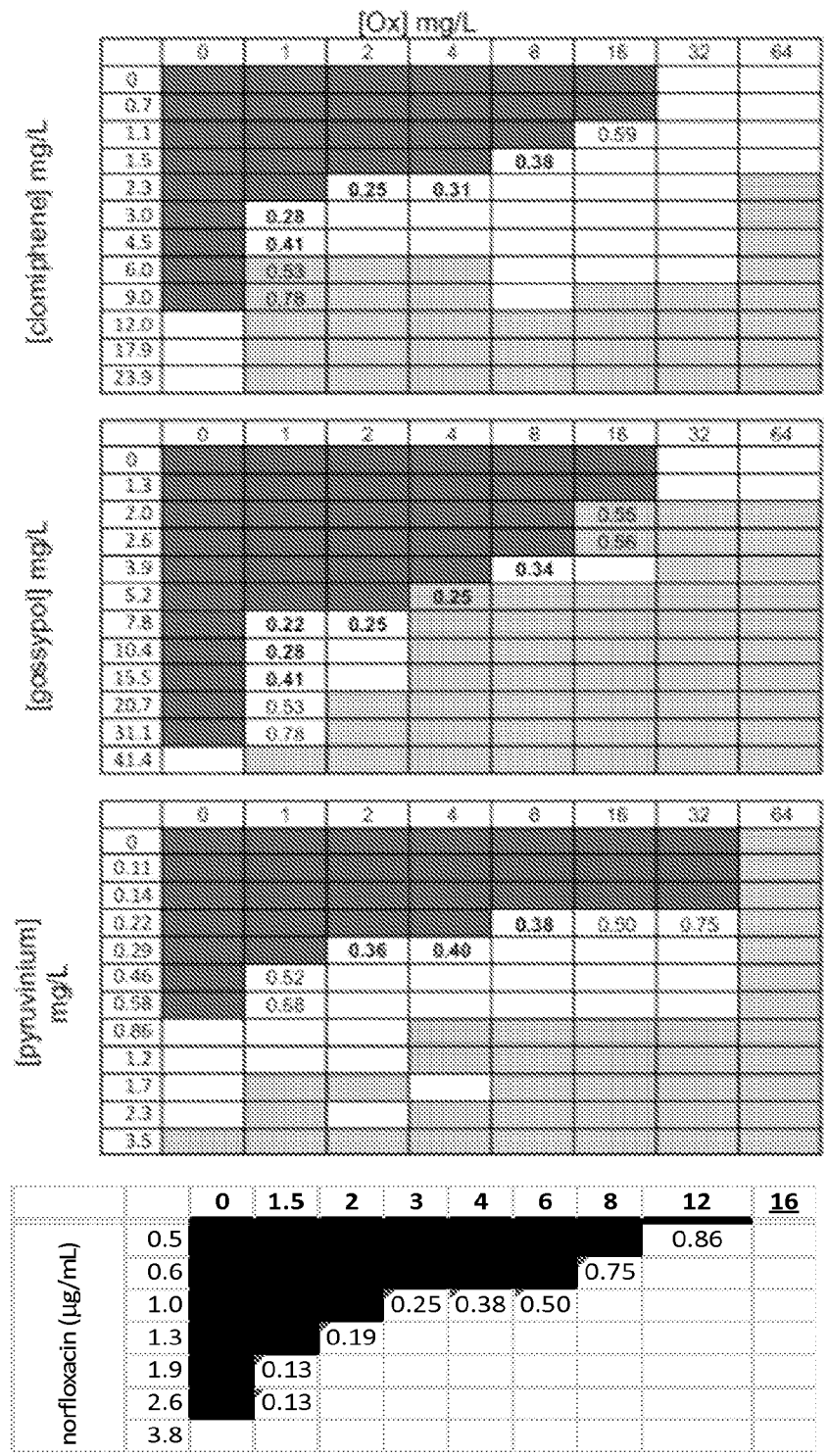
FIG. 6: Checkerboard assay of compounds that potentiated oxacillin. Increasing concentrations of oxacillin (Ox) (μg/L) were arrayed with increasing concentrations of the indicated compound. Dark gray cells indicate wells with turbid growth, white cells indicate no growth; light gray cells indicate 99.9% reduction in colony count. The $FIC_i$ is indicated in each cell representing an MIC. An $FIC_i$ of ≤0.5 defines a synergistic interaction. An $FIC_i > 0.5$ and <0.7 is possibly synergistic.
Figure 7:
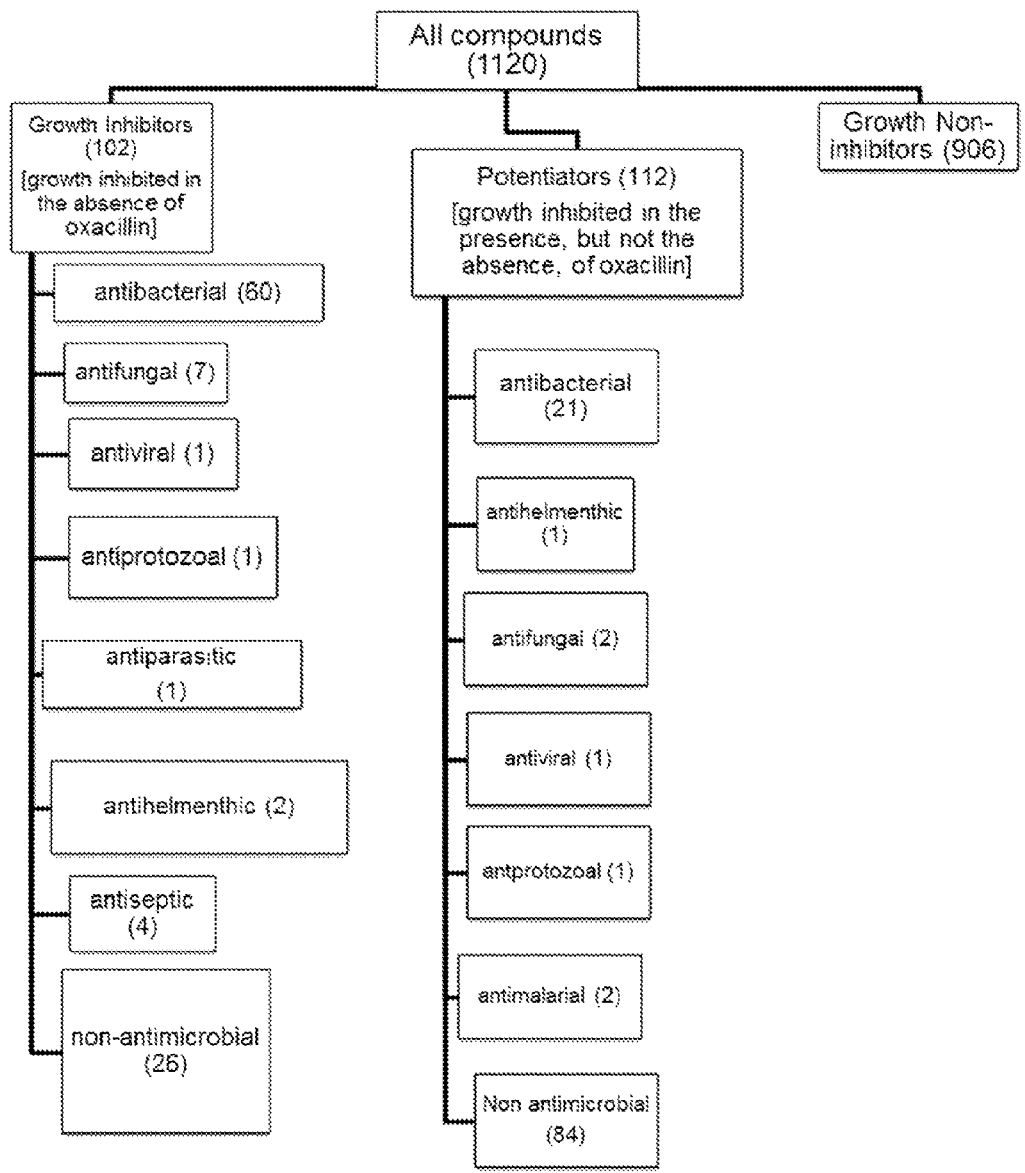
FIG. 7. Classification of compounds in primary screen by medical use. Compounds were first stratified based on their effects on the growth of the test strain. Compounds classified as growth inhibitors were further stratified into known antimicrobials vs other medical uses (See Tables 7 to 10 for further detail).
Figure 8:
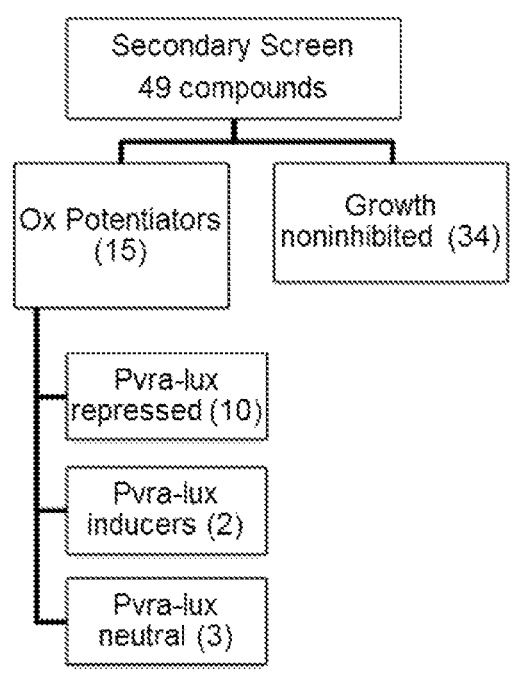
FIG. 8. Classification of compounds' effects on growth and $P_{vra}$-lux expression in the secondary screen.
Figure 9:
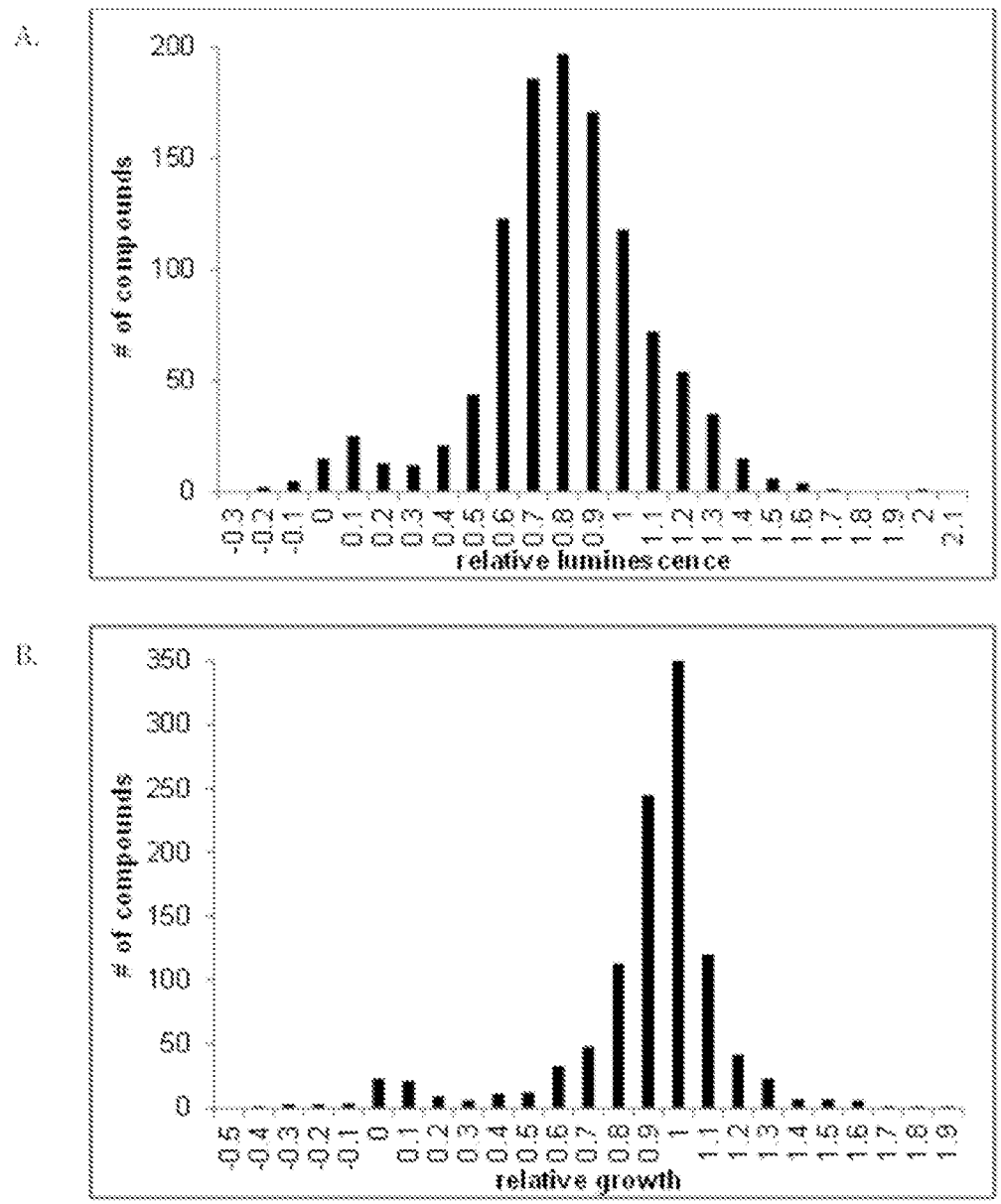
FIG. 9A-B. Distribution of luminescence and $OD_{530}$ values for test compounds in the presence of oxacillin in the primary screen. Relative luminescence (A) and relative growth (B) are shown as bins along the x-axis and the number of compounds in each bin is shown on the y-axis. Relative luminescence and growth were calculated as the ratio of the test value to the average of 49 control values in the presence of oxacillin.

Checkerboard MIC was performed to test the ability of gossypol, pyrvinium, and clomifene to potentiate oxacillin in MRSA strain USA300-isolate 923 (FIG. 6). Norfloxacin and menadione were also tested. To determine the bactericidal effect, in those wells that had an $FIC_i \leq 0.5$, 10 µL from each well was spotted onto TSA plates and incubated overnight at 37° C. A minimal bactericidal concentration (MBC) was defined as any well showing >99.9% killing after the initial 24 hrs, visualized as <5 cfu/spot. The compounds that were considered synergistic, achieving an $FIC_i \leq 0.5$ in at least one combination, were clomiphene citrate, gossypol, pyruvinium pamoate, and norfloxacin. A dose dependent decrease in the MIC of oxacillin was observed for clomiphene citrate, gossypol, and pyruvinium pamoate and norfloxacin (FIG. 6, dark grey wells indicate turbid wells). Additionally, clomiphene, gossypol, and pyruvinium pamoate increased the bactericidal effect of oxacillin (FIG. 6, light grey wells). Menadione did not synergize with oxacillin (data not shown) according to the FICi breakpoint of 0.5; however, menadione at 16 µM decreased the MIC of oxacillin from 32 to 2 mg/L, which is susceptible (Table 3b).

Testing potentiation of oxacillin by compounds in multiple MRSA strains: In order to be considered a synergistic agent in therapy of MRSA infection, it must be effective as a potentiator in diverse MRSA strains. To determine whether the oxacillin potentiators were effective against MRSA strains besides USA300, a single effective concentration of three compounds that were not known as antibiotics—gossypol, pyrvinium and clomiphene—were tested against multiple MRSA genetic backgrounds. Each compound was tested at a single optimal concentration, determined in the checkerboard assays, in combination with various concentrations of oxacillin. The strains included in this panel were from diverse genetic backgrounds as determined by multilocus sequence type (MLST) and contained a variety of SCCmec types. The MICs of oxacillin for these strains in the absence of compound ranged from 2 to 256 mg/L and the $MIC_{50}$ was 16 mg/L. As shown in Table 4, in the presence of clomiphene, gossypol and pyrvinium, the $MIC_{50}$ of oxacillin for this panel of strains, was 0.5, 0.5, and 1 mg/L, respectively. This represents a 32-fold decrease in the oxacillin $MIC_{50}$ for clomiphene and gossypol and a 16-fold decrease when using pyrvinium. The $MIC_{80}$ was 2, 8, and 32 µg/L for clomiphene, gossypol, and pyrvinium, respectively.

TABLE 4

MIC of Ox in combination with compounds in diverse MRSA strains. (ST, sequence type as determined by multilocus sequence typing. SCCmec is the mobile genetic element that carries the mecA gene into the chromosome of S. aureus).

| Strain | | | | MIC Ox in presence of compound | | |
|---|---|---|---|---|---|---|
| Characteristics | | | MIC Ox | Ox + | Ox + | Ox + |
| Isolate ID | SCCmec | ST | Ox (µg/mL) | clom (3.8 µM) | gos (15 µM) | pyr (0.5 µM) |
| Q2461 | VT | 59 | 8 | 0.06 | 0.06 | 0.13 |
| 8227-01 | IV | 87 | 4 | 0.06 | 0.06 | 0.25 |
| 923 | IV | 8 | 16 | 0.5 | 0.5 | 0.5 |
| 8010-01 | IV | 8 | 8 | 0.5 | 0.5 | 0.5 |
| 14315 | IV | 1 | 16 | 0.5 | 4 | 0.5 |
| 13113 | II | 5 | 8 | 0.06 | 0.25 | 1 |
| 2169 | IV | 72 | 16 | 0.25 | 1 | 2 |
| 13354 | IV | 5 | 8 | 0.125 | 0.13 | 16 |
| 1176 | II | 231 | 32 | 0.5 | 1 | 32 |
| 11095 | II | 105 | 128 | 2 | 8 | 256 |
| 8004-01 | III | 239 | 256 | 32 | 128 | 256 |
| | | MIC 50 | 16 | 0.5 | 0.5 | 1 |
| | | MIC 80 | 128 | 2 | 8 | 32 |

Further checkerboard testing of MRSA strain 8004-01 with clomiphene and gossypol combined with oxacillin demonstrated that these compounds approached the synergy breakpoint with an $FIC_i$ of 0.53 and 0.56, respectively (Table 5). Pyrvinium was highly synergistic with oxacillin in strain 11095. Pyrvinium decreased the oxacillin MIC by 128-fold and an $FIC_i$ of 0.26 was obtained.

TABLE 5

FICi's of oxacillin + compounds in strains 8004-1 and 11095

| | | MIC OX | MIC OX (+) | MIC cmpd + mg/L | MIC cmpd alone | FIC Ox | FIC Compound | FICi |
|---|---|---|---|---|---|---|---|---|
| 8004-1 ST239 | Clo | 512 | 16 | 5.2 | 10.4 | .03 | 0.5 | 0.53 |
| | Gos | 512 | 32 | 20 | 40 | .06 | .5 | .56 |
| | Pyr | >256 | >256 | >4 | >4 | ? | ? | ? |
| 11095 | Pyr | 512 | 4 | 4 | 16 | .0078 | 0.25 | .26 |

Since vraSR expression is also induced by vancomycin, the ability of the compounds to potentiate vancomycin in vitro was tested by performing checkerboard assays with a vancomycin intermediate resistant *Staphylococcus aureus* strain, VISA 2283 (MIC vancomycin 16 mg/L); a hetero VISA isolate, hVISA 2275 (MIC of vancomycin of 4 mg/L), and two vanA containing VRSA strains, VRS1 (MIC of vancomycin 1024 mg/L) and VRS2 (MIC of vancomycin 16 mg/L). As shown in the analysis of the checkerboard assays (Table 6), gossypol fully potentiated vancomycin (FIC i<0.5) in hVISA, VISA, VRS2 and VRS1. Pyrvinium partially potentiated vancomycin (FIC i>0.5 and <1.0) in hVISA, and fully potentiated in both of the vanA containing VRSA strains but not in the VISA strain. Clomiphene partially potentiated vancomycin in hVISA, VISA, and VRS1 and it fully potentiated in strain VRS2. For gossypol, the degree of vancomycin potentiation was not dependent on the vancomycin MIC of the strain since pyrvinium was a stronger potentiator in VRS1 (which has a vancomycin MIC of 1024 mg/L without compound) than it was for the VISA strain (which has a vancomycin MIC of 8 in the absence of pyrvinium). In the VRSA strain, the MIC of vancomycin decreased by 64 fold whereas in the VISA strain, pyrvinium decreased the vancomycin MIC by 2 to 4 fold.

TABLE 6

FICs and FICi from checkerboard assays: Clomiphene (Clo), Vancomycin (Van or V), Pyrvinium (Pyr), Gossypol, (Gos). Van+ indicates vancomycin MIC when used in combination with compound, Clo+, Pyr+ or Gps+ signifies MIC of the compound when used in combination with the indicated Van concentration).

| Strain | MIC (mg/L) | | MIC (in combination)* | | FIC | | FICi | fold decrease | Synergy |
|---|---|---|---|---|---|---|---|---|---|
| Clo | Van | Clo | Van+ | Clo+ | Van FIC | Clo FIC | FICi V + Clo | Van MIC | category |
| hVISA 2275 | 4 | 12 | 2 | 1.5 | 0.5 | 0.13 | 0.63 | 2 | partial |
| hVISA 2275 | 4 | 12 | 1 | 6 | 0.25 | 0.5 | 0.75 | 4 | partial |
| VISA 2283 | 8 | 12 | 4 | 3 | 0.5 | 0.25 | 0.75 | 2 | partial |
| VRS2 | 16 | 12 | 1 | 6 | 0.06 | 0.5 | 0.56 | 16 | partial |
| VRS2 | 16 | 12 | 2 | 3 | 0.13 | 0.25 | 0.38 | 8 | synergistic |
| VRS2 | 16 | 12 | 8 | 1.5 | 0.50 | 0.13 | 0.63 | 2 | partial |
| VRS1 | 1024 | 12 | 512 | 3 | 0.50 | 0.25 | 0.75 | 2 | partial |
| | 1024 | 12 | 256 | 6 | 0.25 | 0.5 | 0.75 | 4 | partial |
| Pyr | Van | Pyr | Van+ | Pyr+ | Van FIC | Pyr FIC | FICi V + Py | | |
| hVISA 2275 | 4 | 16 | 2 | 0.56 | 0.50 | 0.04 | 0.54 | 2 | partial |
| VRS2 | 16 | 1.12 | 1 | 0.28 | 0.06 | 0.25 | 0.31 | 16 | synergistic |
| VRS2 | 16 | 1.12 | 2 | 0.14 | 0.13 | 0.13 | 0.25 | 8 | synergistic |
| VRS1 | 1024 | 2.24 | 1 | 1.1 | 0.00 | 0.49 | 0.49 | 1024 | synergistic |
| VRS1 | 1024 | 2.24 | 64 | 0.56 | 0.06 | 0.25 | 0.31 | 16 | synergistic |
| VRS1 | 1024 | 2.24 | 512 | 0.14 | 0.50 | 0.06 | 0.56 | 2 | partial |
| VISA | | | | | | | | | non syn |
| Gos | Van | Gos | Van+ | Gos+ | Van FIC | Gos FIC | FICi V + G | | |
| hVISA 2275 | 4 | 10.4 | 1 | 1.3 | 0.25 | 0.125 | 0.38 | 4 | synergistic |
| VISA 2283 | 8 | 10.4 | 4 | 1.3 | 0.50 | 0.125 | 0.63 | 2 | partial |
| VISA 2283 | 8 | 10.4 | 2 | 5.2 | 0.25 | 0.5 | 0.75 | 4 | partial |
| VRS2 | 16 | 5.2 | 1 | 1.3 | 0.06 | 0.25 | 0.31 | 16 | synergistic |
| VRS1 | 1024 | 20.8 | 16 | 1.3 | 0.02 | 0.0625 | 0.08 | 64 | synergistic |
| VRS1 | 1024 | 20.8 | 1 | 2.6 | 0.001 | 0.125 | 0.13 | 1024 | synergistic |

TABLE 7

Primary Screen Potentiators
(grouped by previously known mode of action/indication)

Analgesic

Fosfosal
Anesthetic

Butacaine
Meprylcaine hydrochloride
Oxethazaine
Anthelmintic

Avermectin B1
Antiarrythmic

Amiodarone hydrochloride
Propafenone hydrochloride
Antiatherosclerotic

Leucomisine
Antibiotic

Azlocillin sodium salt
Bacampicillin hydrochloride
Bacitracin
Cefoperazone dehydrate
Cefotiam hydrochloride
Cephalothin sodium salt
Cinoxacin
D-cycloserine
Doxorubicin hydrochloride
Ethionamide
Furaltadone hydrochloride
Imipenem
Loracarbef
Nalidixic acid sodium salt hydrate
Norfloxacin
Oleandomycin phosphate
Phenethicillin potassium salt
Pivmecillinam hydrochloride
Spectinomycin dihydrochloride
Spiramycin
Sulfamerazine
Anticholinergic Clidinium bromide
Procyclidine hydrochloride
Anticonvulsant Phensuximide
Trimethadione
Antidiabetic Gliquidone
Repaglinide
Antidopaminergic Domperidone
Droperidol
Antifungal Nystatine
Pentamidine isethionate
Antihistamine Cinnarizine
Terfenadine
Trimeprazine tartrate
Antihypertensive Rilmenidine hemifumarate
Antimalarial Artemisinin
Halofantrine hydrochloride
Antimuscarinic Methantheline bromide
Propantheline bromide

TABLE 7-continued

Primary Screen Potentiators
(grouped by previously known mode of action/indication)

Antineoplastic

Mitoxantrone dihydrochloride
Antioxidant

Bergenin monohydrate
Chlorogenic acid
Antiprotozoal

Nifurtimox
Antipsychotic

Bromperidol
Fluspirilen
Pimozide
Promazine hydrochloride
Antispasmodic

Hymecromone
Antitussive

Levopropoxyphene napsylate
Antiulcer

Cisapride
Antiviral

Betulinic acid
Antipsychotic

Clozapine
Asthma

Beclomethasone dipropionate
B-vitamin

Biotin
beta blocker (−)-Levobunolol hydrochloride
(S)-propranolol hydrochloride
Nadolol
blood pressure Guanfacine hydrochloride
calcium channel blocker Fendiline hydrochloride
calcium regulator Calciferol
cardiac glycoside Digoxin
Chemotherapy Daunorubicin hydrochloride
Ifosfamide
contrast medium Iocetamic acid
Iopanoic acid
Ioxaglic acid
Cosmetics Ursolic acid
Diuretic Trichlormethiazide
esophageal ulceration Carbenoxolone disodium salt
estrogen oral contraceptive Ethynylestradiol 3-methyl ether

TABLE 7-continued

Primary Screen Potentiators
(grouped by previously known mode of action/indication)

| |
|---|
| female infertility |
| Clomiphene citrate (Z,E)<br>Flavonol |
| Acacetin<br>Kaempferol<br>GABA receptor antagonist |
| Securinine<br>Glaucoma |
| Methazolamide<br>high blood pressure |
| Benzthiazide<br>Hormone |
| Diethylstilbestrol<br>Hypercholesterolemia |
| Beta-sistosterol<br>Hyperthyroidism |
| Liothyronine<br>Hypnotic |
| Pyrithyldione<br>Immunosuppressant |
| Cyclosporin A<br>Laxative |
| Bisacodyl<br>mast cell stabilizer |
| Cromolyn disodium salt<br>NSAID |
| Indoprofen<br>Suprofen<br>Tenoxicam<br>opioid agonist |
| (−)-Eseroline fumarate salt<br>Osteoporosis |
| Raloxifene hydrochloride<br>Other |
| Chicago sky blue 6B<br>Phenol |
| Resveratrol<br>phenol antioxidant |
| Catechin-(+,−) hydrate<br>phosphodiesterase inhibitor |
| Bucladesine sodium salt<br>progestagen hormone |
| Lynestrenol<br>proton pump unhibitor |
| Lansoprazole<br>rheumatoid arthritis |
| Amiprilose hydrochloride<br>senile dementia |
| Meclofenoxate hydrochloride<br>SSRI antidepressant |
| Paroxetine Hydrochloride |

TABLE 7-continued

Primary Screen Potentiators
(grouped by previously known mode of action/indication)

| |
|---|
| Steroid |
| Budesonide<br>Digitoxigenin<br>synthetic vitamin K |
| Menadione<br>toxin (animal cells) |
| Sanguinarine<br>urinary retention |
| Bethanechol chloride<br>Undefined |
| Oxalamine citrate salt<br>Tetrahydroxy-1,4-quinone monohydrate |

TABLE 8

Primary Screen Potentiators
(grouped by vraSR mechanism and mode of action/indication)

| |
|---|
| vraSR neutral |
| Analgesic |
| Fosfosal<br>Anesthetic |
| Meprylcaine hydrochloride<br>Oxethazaine<br>Anthelmintic |
| Avermectin B1<br>Antiarrythmic |
| Propafenone hydrochloride<br>antiatherosclerotic |
| Leucomisine<br>Antibiotic |
| Bacampicillin hydrochloride<br>Bacitracin<br>D-cycloserine<br>Doxorubicin hydrochloride<br>Ethionamide<br>Imipenem<br>Loracarbef<br>Nalidixic acid sodium salt hydrate<br>Pivmecillinam hydrochloride<br>anticholinergic |
| Procyclidine hydrochloride<br>anticonvulsant |
| Phensuximide<br>Trimethadione<br>Antidiabetic |
| Gliquidone<br>Repaglinide<br>antidopaminergic |
| Domperidone<br>Antifungal |
| Nystatine<br>Pentamidine isethionate<br>Antihistamine |
| Cinnarizine<br>Terfenadine |

TABLE 8-continued

Primary Screen Potentiators
(grouped by vraSR mechanism and mode of action/indication)

antihypertensive

Rilmenidine hemifumarate
Antimalarial

Artemisinin
Halofantrine hydrochloride
antimuscarinic

Methantheline bromide
Propantheline bromide
Antineoplastic

Mitoxantrone dihydrochloride
Antioxidant

Bergenin monohydrate
Chlorogenic acid
Antipsychotic

Bromperidol
Pimozide
Antispasmodic

Hymecromone
Antitussive

Levopropoxyphene napsylate
Antiulcer

Cisapride
Antiviral

Betulinic acid
antipsychotic

Clozapine
b-vitamin

Biotin
beta blocker (−)-Levobunolol hydrochloride
(S)-propranolol hydrochloride
Nadolol
calcium channel blocker Fendiline hydrochloride
calcium regulator Calciferol
cardiac glycoside Digoxin
Chemotherapy Daunorubicin hydrochloride
Ifosfamide
contrast medium Iocetamic acid
Iopanoic acid
Ioxaglic acid
esophageal ulceration Carbenoxolone disodium salt
female infertility Clomiphene citrate (Z,E)
Flavonol Kaempferol
GABA receptor antagonist Securinine TABLE 8-continued Primary Screen Potentiators
(grouped by vraSR mechanism and mode of action/indication)

Glaucoma

Methazolamide
hypercholesterolemia

Beta-sistosterol
Hypnotic

Pyrithyldione
immunosuppressant

Cyclosporin A
Laxative

Bisacodyl
mast cell stabilizer

Cromolyn disodium salt
NSAID

Suprofen
Tenoxicam
opioid agonist (−)-Eseroline fumarate salt
Other

Chicago sky blue 6B
Phenol

Resveratrol
phenol antioxidant

Catechin-(+,−) hydrate
proton pump unhibitor

Lansoprazole
rheumatoid arthritis

Amiprilose hydrochloride
SSRI antidepressant

Paroxetine Hydrochloride
Steroid

Budesonide
Digitoxigenin
urinary retention

Bethanechol chloride
Undefined

Tetrahydroxy-1,4-quinone monohydrate vraSR repressor

Anesthetic

Butacaine
Antibiotic

Azlocillin sodium salt
Cinoxacin
Furaltadone hydrochloride
Norfloxacin
Oleandomycin phosphate
Phenethicillin potassium salt
Spectinomycin dihydrochloride
Spiramycin
Sulfamerazine
anticholinergic Clidinium bromide
antidopaminergic Droperidol

TABLE 8-continued

Primary Screen Potentiators
(grouped by vraSR mechanism and mode of action/indication)

Antiprotozoal

Nifurtimox
Antipsychotic

Promazine hydrochloride
Asthma

Beclomethasone dipropionate
blood pressure

Guanfacine hydrochloride
Cosmetics

Ursolic acid
Diuretic

Trichlormethiazide
estrogen oral contraceptive

Ethynylestradiol 3-methyl ether
Flavonol

Acacetin
high blood pressure

Benzthiazide
Hormone

Diethylstilbestrol
hyperthyroidism

Liothyronine
NSAID

Indoprofen
Osteoporosis

Raloxifene hydrochloride
phosphodiesterase inhibitor

Bucladesine sodium salt
progestagen hormone

Lynestrenol
senile dementia

Meclofenoxate hydrochloride
synthetic vitamin K

Menadione
toxin (animal cells)

Sanguinarine
Undefined

Oxalamine citrate salt vraSR stimulating

Antiarrythmic

Amiodarone hydrochloride
Antibiotic

Cefoperazone dihydrate
Cefotiam hydrochloride
Cephalothin sodium salt
Antihistamine Trimeprazine tartrate
Antipsychotic Fluspirilen

TABLE 9

Primary Screen Growth Inhibitors
(grouped by mode of action/indication)

Antianginal

Perhexiline maleate
Trimetazidine dihydrochloride
Antibiotic

Alexidine dihydrochloride
Amikacin hydrate
Cefalonium
Cefamandole sodium salt
Cefazolin sodium salt
Cefepime hydrochloride
Cefixime
Cefmetazole sodium salt
Ceforanide
Cefotaxime sodium salt
Cefotetan
Cefoxitin sodium salt
Cefsulodin sodium salt
Cefuroxime sodium salt
Cephalexin monohydrate
Chlortetracycline hydrochloride
Ciprofloxacin hydrochloride
Clindamycin hydrochloride
Cloxacillin sodium salt
Demeclocycline hydrochloride
Dicloxacillin sodium salt
Dirithromycin
Doxycycline hyclate
Enoxacin
Erythromycin
Florfenicol
Flucloxacillin sodium
Flumequine
Fusidic acid sodium salt
Josamycin
Lasalocid sodium salt
Lincomycin hydrochloride
Lomefloxacin hydrochloride
Meclocycline sulfosalicylate
Meropenem
Methacycline hydrochloride
Midecamycin
Minocycline hydrochloride
Monensin sodium salt
Moxalactam disodium salt
Nafcillin sodium salt monohydrate
Nitrofural
Novobiocin sodium salt
Ofloxacin
Oxolinic acid
Oxytetracycline dihydrate
Pyrazinamide
Rifabutin
Rifampicin
Roxithromycin
Streptozotocin
Sulfamethizole
Sulfamonomethoxine
Tetracycline hydrochloride
Thiostrepton
Ticarcillin sodium
Tobramycin
Trimethoprim
Troleandomycin
Vancomycin hydrochloride
Anticoagulant Dicumarol
Antidepressant Maprotiline hydrochloride
Antieleptic Vigabatrin

TABLE 9-continued

Primary Screen Growth Inhibitors
(grouped by mode of action/indication)

Antifungal

Butoconazole nitrate
Clioquinol
Clotrimazole
Naftifine hydrochloride
Sertaconazole nitrate
Sulconazole nitrate
Antihelmintic Niclosamide
Pyrvinium pamoate
Antihistamine Ketotifen fumarate
antiinflammatory Clofazimine
Antimicrobial Atovaquone
Antiparasitic Ivermectin
Antiprotozoal Ronidazole
Antipsychotic Chlorprothixene hydrochloride
Antiseptic Benzethonium chloride
Chlorhexidine
Dequalinium dichloride
Methyl benzethonium chloride
Antiviral Trifluridine
cerebral blood-flow Vinpocetine
cholesterol reducer Fenofibrate
COX-2 inhibitor Tomatidine
Detergent Thonzonium bromide
estrogen receptor antagonist Tamoxifen citrate
gout treatment Benzbromarone
Hypolipidemic Benfluorex hydrochloride
immunosuppressant Mycophenolic acid
increases circulation Pentoxifylline
joint pain Meclofenamic acid sodium salt monohydrate
muscle pain Niflumic acid
muscle relaxant Methocarbamol
Norcyclobenzaprine

NSAID

Tolfenamic acid
Phenol

Gossypol
Photosensitizer

Verteporfin
Steroid

Triamcinolone
Undefined

Isoquinoline, 6,7-dimethoxy-1-methyl-1,2,3,4-tetrahydro, hydrochloride

TABLE 10

Primary Screen Growth inhibitors Not Included in Secondary Screen
(grouped by mode of action/indication)

Anthelmintic

Niclosamide
Antianginal

Perhexiline maleate
Trimetazidine dihydrochloride
Anticoagulant

Dicumarol
Antidepressant

Maprotiline hydrochloride
Antieleptic

Vigabatrin
Antifungal

Butoconazole nitrate
Clioquinol
Clotrimazole
Naftifine hydrochloride
Sertaconazole nitrate
Sulconazole nitrate
Antihistamine Ketotifen fumarate
antiinflamitory Clofazimine
Antimicrobial Atovaquone
Antiparasitic Ivermectin
Antiprotozoal Ronidazole
Antipsychotic Chlorprothixene hydrochloride
Antiseptic Benzethonium chloride
Chlorhexidine
Dequalinium dichloride
Methyl benzethonium chloride
Antiviral Trifluridine

TABLE 10-continued

Primary Screen Growth inhibitors Not Included in Secondary Screen (grouped by mode of action/indication)

cerebral blood-flow

Vinpocetine
cholesterol reducer

Fenofibrate
COX-2 inhibitor

Tomatidine
Detergent

Thonzonium bromide
estrogen receptor antagonist

Tamoxifen citrate
gout treatment

Benzbromarone
Hypolipidemic

Benfluorex hydrochloride
immunosuppressant

Mycophenolic acid
increases circulation

Pentoxifylline
joint pain

Meclofenamic acid sodium salt monohydrate
muscle pain

Niflumic acid
muscle relaxant

Methocarbamol
Norcyclobenzaprine
NSAID

Tolfenamic acid
Photosensitizer

Verteporfin
Steroid

Triamcinolone
(blank)

Isoquinoline, 6,7-dimethoxy-1-methyl-1,2,3,4-tetrahydro, hydrochloride

TABLE 11

Fifty-seven compounds that potentiated oxacillin in the primary screen but were vraSR neutral and were not tested in the secondary screen (excludes 8 known antibiotics)

| Use and chemical name | Column Labels VraSR Neutral N = 57* |
|---|---|
| analgesic | 1 |
| Fosfosal | 1 |
| anesthetic | 2 |
| Meprylcaine hydrochloride | 1 |
| Oxethazaine | 1 |
| anthelmintic | 1 |
| Avermectin B1 | 1 |
| antiarrythmic | 1 |
| Propafenone hydrochloride | 1 |
| antiatherosclerotic | 1 |
| Leucomisine | 1 |
| anticholinergic | 1 |
| Procyclidine hydrochloride | 1 |
| anticonvulsant | 2 |
| Phensuximide | 1 |
| Trimethadione | 1 |
| antidiabetic | 2 |
| Gliquidone | 1 |
| Repaglinide | 1 |
| antifungal | 1 |
| Pentamidine isethionate | 1 |
| antihistamine | 1 |
| Terfenadine | 1 |
| antihypertensive | 1 |
| Rilmenidine hemifumarate | 1 |
| antimalarial | 2 |
| Artemisinin | 1 |
| Halofantrine hydrochloride | 1 |
| antimuscarinic | 2 |
| Methantheline bromide | 1 |
| Propantheline bromide | 1 |
| antioxidant | 2 |
| Bergenin monohydrate | 1 |
| Chlorogenic acid | 1 |
| antipsychotic | 2 |
| Bromperidol | 1 |
| Pimozide | 1 |
| antispasmodic | 1 |
| Hymecromone | 1 |
| antitussive | 1 |
| Levopropoxyphene napsylate | 1 |
| antiulcer | 1 |
| Cisapride | 1 |
| antypsychotic | 1 |
| Clozapine | 1 |
| b-vitamin | 1 |
| Biotin | 1 |
| beta blocker | 3 |
| (−)-Levobunolol hydrochloride | 1 |
| (S)-propranolol hydrochloride | 1 |
| Nadolol | 1 |
| calcium channel blocker | 1 |
| Fendiline hydrochloride | 1 |
| cardiac glycoside | 1 |
| Digoxin | 1 |
| chemotherapy | 1 |
| Ifosfamide | 1 |
| contrast medium | 3 |
| locetamic acid | 1 |
| lopanoic acid | 1 |
| loxaglic acid | 1 |
| esophageal ulceration | 1 |
| Carbenoxolone disodium salt | 1 |
| flavonol | 1 |
| Kaempferol | 1 |
| GABA receptor antagonist | 1 |
| Securinine | 1 |
| glaucoma | 1 |
| Methazolamide | 1 |
| hypercholesterolemia | 1 |
| Beta-sistosterol | 1 |
| hypnotic | 1 |
| Pyrithyldione | 1 |
| immunosuppressant | 1 |
| Cyclosporin A | 1 |
| laxative | 1 |
| Bisacodyl | 1 |
| mast cell stabilizer | 1 |
| Cromolyn disodium salt | 1 |
| NSAID | 2 |
| Suprofen | 1 |
| Tenoxicam | 1 |
| opioid agonist | 1 |
| (−)-Eseroline fumarate salt | 1 |
| other | 1 |
| Chicago sky blue 6B | 1 |

TABLE 11-continued

Fifty-seven compounds that potentiated oxacillin in the primary screen but were vraSR neutral and were not tested in the secondary screen (excludes 8 known antibiotics)

| Use and chemical name | Column Labels VraSR Neutral N = 57* |
|---|---|
| phenol | |
| Resveratrol | 1 |
| phenol antioxidant | 1 |
| Catechin-(+,−) hydrate | 1 |
| proton pump unhibitor | |
| Lansoprazole | 1 |
| rheumatoid arthritis | |
| Amiprilose hydrochloride | 1 |
| SSRI antidepressant | |
| Paroxetine Hydrochloride | 1 |
| steroid | |
| Budesonide | 1 |
| urinary retention | |
| Bethanechol chloride | 1 |
| (blank) | |
| Tetrahydroxy-1,4-quinone monohydrate | 1 |
| Grand Total | 57 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Boyle-Vavra et al., *Antimicrob Agents Chemother.*, 57(1): 83-95, 2012.
Boyle-Vavra et al., *FEMS Microbiology Letters*, 262(2):163-171, 2006.
Francis K P et al., *Infection and Immunity*, 68(6):3594-3600, 2000.
Jo, D. S., et al., *Antimicrob. Agents Chemother.*, 55:2818-23, 2011.
Livak K J et al., *Methods*, 25(4):402-408, 2001.
Montgomery C P et al., *The Journal of Infectious Diseases*, 198(4):561-570, 2008.
Williams & Waltho, *J. Am. Chem. Soc.* 111:2475-80, 1994.
Williams & Waltho, *Biochem. Pharmacology* 37(1):133-31, 1988.
Yin et al., *Antimicrobial Agents and Chemotherapy*, 50(1): 336-343, 2006.

The invention claimed is:

1. A method for inhibiting a *staphylococcus* infection comprising administering to a subject having a *staphylococcus* infection or at risk of a *staphylococcus* infection:
   (a) oxacillin, and;
   (b) an antibiotic potentiator, wherein the antibiotic potentiator is clomifene, gossypol, menadione, pyrvinium, or a prodrug or salt thereof.

2. The method of claim 1, wherein the subject has been tested for a *staphylococcus* infection.

3. The method of claim 1, wherein the *staphylococcus* infection is Staphylococcus aureus.

4. The method of claim 1, wherein the *staphylococcus* infection is methicillin resistant Staphylococcus aureus (MRSA).

5. The method of claim 1, wherein the subject has or is at risk for native valve endocarditis or prosthetic valve endocarditis.

6. The method of claim 5, wherein the subject is administered about 2-3 g of oxacillin intravenously every 4 to 6 hours.

7. The method of claim 1, wherein the subject has or is at risk for joint infection, meningitis, osteomyelitis, pneumonia, septicemia, sinusitis, or skin or soft tissue infection.

8. The method of claim 1, further comprising administering a second antibiotic.

9. The method of claim 8, wherein the second antibiotic is gentamicin or rifampin.

10. The method of claim 1, wherein the subject is a pediatric patient.

11. The method of claim 1, whereby administration to a subject is oral, sublingual, sublabial, gastrointestinal, rectal, epicutaneous (topical), intradermal, subcutaneous, nasal, intravenous, intraarterial, intramuscular, intracardiac, intraosseous, intrathecal, intraperitoneal, intravesical, intravitreal, intracavernous, intravaginal, intrauterine, epidural, intracerebral and/or intracerebroventricular.

12. The method of claim 1, wherein administration is topical, enteral, or parenteral.

13. The method of claim 1, wherein administration is by application onto the skin, inhalation, an enema, eye drops, ear drops, absorption across mucosal membranes, the mouth, a gastric feeding tube, a duodenal feeding tube, a suppository, an injection into a vein, an injection into an artery, an injection into the bone marrow, an injection into muscle tissue, an injection into the brain, an injection into the cerebral ventricular system or an injection under the skin.

14. The method of claim 1, wherein the antibiotic and the antibiotic potentiator are administered in the same composition.

15. The method of claim 1, wherein the antibiotic potentiator is selected from clomiphene, gossypol, and pyrvinium.

* * * * *

SEQUENCE LISTING

```
<160> NUMBER OF SEQ ID NOS: 8

<210> SEQ ID NO 1
<211> LENGTH: 32
<212> TYPE: DNA
<213> ORGANISM: Artificial Sequence
<220> FEATURE:
<223> OTHER INFORMATION: Synthetic Primer

<400> SEQUENCE: 1
aaagaattct gaaggtatgg tattagctat tg                                    32

<210> SEQ ID NO 2
<211> LENGTH: 31
<212> TYPE: DNA
<213> ORGANISM: Artificial Sequence
<220> FEATURE:
<223> OTHER INFORMATION: Synthetic Primer

<400> SEQUENCE: 2
aaaggatccg ttgatgtcga tgatatgttt g                                     31

<210> SEQ ID NO 3
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' fluorescent reporter
<220> FEATURE:
```

```
<221> NAME/KEY: misc_feature
<222> LOCATION: (10)..(10)
<223> OTHER INFORMATION: ZEN Internal Quencher
<220> FEATURE:
<221> NAME/KEY: misc_feature
<222> LOCATION: (26)..(26)
<223> OTHER INFORMATION: 3' quencher dye

<400> SEQUENCE: 3
ttgccaaagc ccatgagttg aagcca                                              26

<210> SEQ ID NO 4
<211> LENGTH: 24
<212> TYPE: DNA
<213> ORGANISM: Artificial Sequence
<220> FEATURE:
<223> OTHER INFORMATION: Synthetic Primer

<400> SEQUENCE: 4
tagttggtga aggcgcttct ggta                                                24

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer

<400> SEQUENCE: 5
tcgtcgcttc tacaccatcc atgt                                                24

<210> SEQ ID NO 6
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Cy5 dye
<220> FEATURE:
<221> NAME/KEY: misc_feature
<222> LOCATION: (26)..(26)
<223> OTHER INFORMATION: 3' quencher dye IAbRQSp

<400> SEQUENCE: 6
aaatgggacg tccagctgtc gaagtt                                              26

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
ccgccaaatt taccaccagc atgt                                                24

<210> SEQ ID NO 8
<211> LENGTH: 24
<212> TYPE: DNA
<213> ORGANISM: Artificial Sequence
<220> FEATURE:
<223> OTHER INFORMATION: Synthetic Primer
```

```
<400> SEQUENCE: 8
aacggacgtg gtatcccagt tgat                                      24
```